(12) United States Patent
Bagal et al.

(10) Patent No.: US 9,079,878 B2
(45) Date of Patent: Jul. 14, 2015

(54) (4-PHENYLIMIDAZOL-2-YL) ETHYLAMINE DERIVATIVES USEFUL AS SODIUM CHANNEL MODULATORS

(71) Applicant: Pfizer Limited, Sandwich (GB)

(72) Inventors: Sharanjeet Kaur Bagal, Great Abington (GB); Mark Ian Kemp, Sandwich (GB); Duncan Charles Miller, Sandwich (GB); Yoshihisa Murata, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 14/351,893

(22) PCT Filed: Oct. 15, 2012

(86) PCT No.: PCT/IB2012/055610
§ 371 (c)(1),
(2) Date: Apr. 15, 2014

(87) PCT Pub. No.: WO2013/061205
PCT Pub. Date: May 2, 2013

(65) Prior Publication Data
US 2014/0296313 A1 Oct. 2, 2014

Related U.S. Application Data

(60) Provisional application No. 61/551,628, filed on Oct. 26, 2011.

(51) Int. Cl.
*A61K 31/4178* (2006.01)
*C07D 405/06* (2006.01)

(52) U.S. Cl.
CPC .......... *C07D 405/06* (2013.01); *A61K 31/4178* (2013.01)

(58) Field of Classification Search
CPC ................ C07D 405/06; A61K 31/4178
USPC ......... 514/397, 365, 374, 378, 396, 422, 966; 548/315, 205; 424/488
See application file for complete search history.

(56) References Cited

U.S. PATENT DOCUMENTS

| | | | |
|---|---|---|---|
| 6,106,864 A | | 8/2000 | Dolan et al. |
| 2005/0038087 A1 | | 2/2005 | De Lassauniere et al. |
| 2005/0234118 A1 | | 10/2005 | Bigg et al. |
| 2005/0267095 A1* | | 12/2005 | Bernardelli et al. ..... 514/210.01 |
| 2006/0199779 A1 | | 9/2006 | Goregaoker et al. |
| 2011/0046129 A1 | | 2/2011 | Thaler et al. |

FOREIGN PATENT DOCUMENTS

| | | |
|---|---|---|
| WO | 0035298 | 6/2000 |
| WO | 2002063656 | 10/2002 |
| WO | 2008047229 | 4/2008 |
| WO | 2008118758 | 10/2008 |
| WO | 2008135826 | 11/2008 |
| WO | 2008135830 | 11/2008 |
| WO | 2009012242 | 1/2009 |

OTHER PUBLICATIONS

Hubner, C.A., et al., "Ion channel diseases", Human Molecular Genetics, Oct. 2002, pp. 2435-2445, 11(20).
Yogeeswari, P., et al., "Ion Channels as Important Targets for Antiepileptic Drug Design", Current Drug Targets, Oct. 2004, pp. 589-602, 5(7).
Noble, D., "Unraveling the genetics and mechanisms of cardiac arrhythmia", Proceedings National Academy of Science USA, Apr. 30, 2002, pp. 5755-5756, 99(9).
Cannon, S.C., "Spectrum of sodium channel disturbances in the nondystrophic myotonias and periodic paralyses", Kidney International, Mar. 2000, pp. 772-779, 57(3).
Wood, J.N., et al., "Voltage-Gated Sodium Channels and Pain Pathways", Journal Neurobiology, Oct. 2004, pp. 55-71, 61(1).
Akopian, A. N., et al., "A tetrodotoxin-resistant voltage-gated sodium channel expressed by sensory neurons", Nature, Jan. 18, 1996, pp. 257-262, 379(6562).
Rabert, D.K., et al., "A tetrodotoxin-resistant voltage-gated sodium channel from human dorsal root ganglia, hPN3/SCN10A", Pain, Nov. 1, 1998, pp. 107-114, 78(2).
Akopian, A.N., et al., "The tetrodotoxin-resistant sodium channel SNS has a specialized function in pain pathways", Nature Neuroscience, 1999, pp. 541-548, 2(6).
Lai, J., et al., "Inhibition of neuropathic pain by decreased expression of the tetrodotoxin-resistant sodium channel, NaV1.8", Pain, Jan. 2002, pp. 143-152, 95(1-2).
Coward, K., et al., "Immunolocalization of SNS/PN3 and NaN/SNS2 sodium channels in human pain states", Pain, Mar. 1, 2000, pp. 41-50, 85(1-2).
Yiangou, Y., et al., "SNS/PN3 and SNS2/NaN sodium channel-like immunoreactivity in human adult and neonate injured sensory nerves", FEBS Letters, Feb. 11, 2000, pp. 249-252, 467 (2-3).
Bucknill, A.T., et al., "Nerve Fibers in Lumbar Spine Structures and Injured Spinal Roots Express the Sensory Neuron-Specific Sodium Channels SNS/PN2 and NaN/SNS2", Spine, Jan. 15, 2002, pp. 135-140, 27(2).

(Continued)

Primary Examiner — Joseph Kosack
Assistant Examiner — Amanda L Aguirre
(74) Attorney, Agent, or Firm — Richard V. Zanzalari

(57) ABSTRACT

The present invention is directed to imidazole derivatives, to their use in medicine, to compositions containing them, to processes for their preparation and to intermediates used in such processes. More particularly the invention relates to a new imidazole $Na_v1.8$ modulators of formula (I):

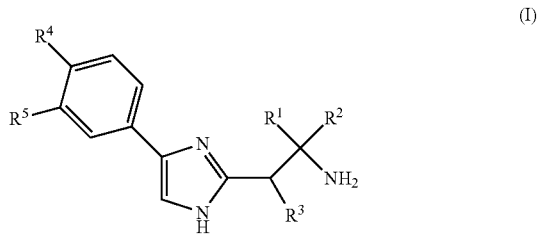

(I)

or a pharmaceutically acceptable salt thereof, wherein $R^1$, $R^2$, $R^3$, $R^4$ and $R^5$ are as defined in the description. $Na_v1.8$ modulators are useful in the treatment of a wide range of disorders, particularly pain.

11 Claims, No Drawings

(56) References Cited

OTHER PUBLICATIONS

Shembalkar, P.K., et al., "Increased sodium channel SNS/PN3 immunoreactivity in a causalgic finger", European Journal of Pain, Jun. 2001, pp. 319-323, 5(3).

Laird, J., et al., "Deficits in Visceral Pain and Referred Hyperalgesia in Nav1.8 (SNS/PN3)-Null Mice", Journal of Neuroscience, Oct. 1, 2002, pp. 8352-8356, 22(19).

Black, J.A., et al., "Abnormal expression of SNS/PN3 sodium channel in cerebellar Purkinje cells following loss of myelin in the taiep rat", NeuroReport, Apr. 6, 1999, pp. 913-918, 10(5).

Almarsson, Ö., et al., "Crystal engineering of the composition of pharmaceutical phases. Do pharmaceutical co-crystals represent a new path to improved medicines", Chemical Communication, 2004, pp. 1889-1896, 17.

Haleblain, J., "Characterization of Habits and Crystalline Modification of Solids and Their Pharmaceutical Applications", Journal Pharmaceutical Science, Aug. 1975, pp. 1269-1288, 64(8).

Finnin, B., et al., "Transdermal Penetration Enhancers: Applications, Limitations, and Potential", Journal of Pharmaceutical Science, Oct. 1999, pp. 955-958, 88(10).

Millan, M.J., "The induction of pain: an integrative review", Progress in Neurobiology, Jan. 1999, pp. 1-164, 57(1).

Woolf, C.J., et al., "Neuronal Plasticity: Increasing the Gain in Pain", Science, Jun. 9, 2000, pp. 1765-1768, 288 (5472).

Woolf, C.J., et al., "Neuropathic pain: aetiology, symptoms, mechanisms, and management", Lancet, 1999, pp. 1959-1964, 353(1968).

Woolf, C.J., et al., "Implications of recent advances in the understanding of pain pathophysiology for the assessment of pain in patients", Pain, Aug. 1999, pp. S141-S147, Supplemental 6, vol. 82.

Houge, J.H., et al., "Pathophysiology and First-Line Treatment of Osteoarthritis", Annals Pharmacotherapy, Apr. 2002, pp. 679-686, 36(4).

PCT/IB2012/055610, International Search Report and Written Opinion, mailed Apr. 12, 2013, 12 pages.

Liang, A., et al., "Fast-dissolving intraorall drug delivery systems", Expert Opinion in Therapeutic Patents, Jun. 2001, pp. 981-986, 11(6).

Black, J.A., et al., "Sensory neuron-specific sodium channel SNS is abnormally expressed in the brains of mice with experimental allergic encephalomyelitis and humans with multiple sclerosis", Proceedings of National Academy of Science USA, Oct. 10, 2000, pp. 11598-11602, 97(21).

Costa Rica Patent application No. 2014-0185, opposition document, received Sep. 24, 2014, 11 pages.

Herold, K.F., et al., "Isoflurane Inhibits the Tetrodotoxin-resistant Voltage-gated Sodium Channel Nav1.8", Anesthesiology, Sep. 2009, pp. 591-599, 111(3).

Chevrier, P., et al., "Differential modulation of Nav 1.7 and Nav1.8 peripheral nerve sodium channels by the local anesthetic lidocaine", British Journal of Pharmacology, 2004, pp. 576-584, 142(3).

China Patent Application No. 201260052591.6 Office Action mailed Feb. 26, 2015, 10 pages.

\* cited by examiner

(4-PHENYLIMIDAZOL-2-YL) ETHYLAMINE DERIVATIVES USEFUL AS SODIUM CHANNEL MODULATORS

This application is a national stage application under 35 U.S.C. 371 of PCT/IB2012/055610, filed on Oct. 15, 2012, which claims the benefit of U.S. Provisional Patent Application No. 61/551,628, filed on Oct. 26, 2011, the disclosure of which is hereby incorporated by reference in its entirety.

FIELD OF THE INVENTION

The invention relates to imidazole derivatives. More particularly, this invention relates to derivatives of (4-phenylimidazol-2-yl)ethylamine, to their use in medicine, to compositions containing them, to processes for their preparation and to intermediates used in such processes.

BACKGROUND

The imidazole derivatives of the present invention are sodium channel modulators. In particular they are modulators of the $Na_V1.8$ sodium channel. Preferred imidazole derivatives of the invention show an affinity for the $Na_V1.8$ channel which is greater than their affinity for other sodium channels such as the $Na_V1.5$ sodium channel and the tetrodotoxin-sensitive sodium channels (TTX-S). The imidazole derivatives of the invention have a number of therapeutic applications and potential therapeutic applications. In particular they are useful in the treatment of pain.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C. A., Jentsch T. J., *Hum. Mol. Genet.*, 11(20): 2435-45 (2002) for a general review of inherited ion channel disorders) including epilepsy (Yogeeswari et al., *Curr. Drug Targets,* 5(7): 589-602 (2004)), arrhythmia (Noble D., *Proc. Natl. Acad. Sci. USA,* 99(9): 5755-6 (2002)) myotonia (Cannon, S. C., *Kidney Int.* 57(3): 772-9 (2000)), and pain (Wood, J. N. et al., *J. Neurobiol.,* 61(1): 55-71 (2004)).

There are currently at least nine known members of the family of voltage-gated sodium channel (VGSC) alpha subunits. Names for this family include SCNx, SCNAx, and $Na_Vx.x$. The VGSC family has been phylogenetically divided into two subfamilies $Na_V1.x$ (all but SCN6A) and $Na_V2.x$ (SCN6A). The $Na_V1.x$ subfamily can be functionally subdivided into two groups, those which are sensitive to blocking by tetrodotoxin (TTX-sensitive or TTX-S) and those which are resistant to blocking by tetrodotoxin (TTX-resistant or TTX-R).

The $Na_V1.8$ channel is a voltage-gated sodium channel which is expressed in nociceptors, the sensory neurones responsible for transducing painful stimuli. The rat channel and the human channel were cloned in 1996 and 1998 respectively (*Nature* 1996; 379: 257-262; *Pain* 1998 (November); 78(2):107-114). The $Na_V1.8$ channel was previously known as SNS (sensory neurone specific) and PN3 (peripheral nerve type 3). The $Na_V1.8$ channel is atypical in that it shows resistance to the blocking effects of the puffer fish toxin tetrodotoxin and it is believed to underlie the slow-voltage-gated and tetrodotoxin-resistant (TTX-R) sodium currents recorded from dorsal root ganglion neurones. The closest molecular relative to the $Na_V1.8$ channel is the $Na_V1.5$ channel, which is the cardiac sodium channel, with which it shares approximately 60% homology. The $Na_V1.8$ channel is expressed most highly in the 'small cells' of the dorsal root ganglia (DRG). These are thought to be the C- and A-delta cells which are the putative polymodal nociceptors, or pain sensors. Under normal conditions, the $Na_V1.8$ channel is not expressed anywhere other than subpopulations of DRG neurones. The $Na_V1.8$ channels are thought to contribute to the process of DRG sensitisation and also to hyperexcitability due to nerve injury. Inhibitory modulation of the $Na_V1.8$ channels is aimed at reducing the excitability of nociceptors, by preventing them from contributing to the excitatory process.

Studies have shown that $Na_V1.8$ knock-out leads to a blunted pain phenotype, mostly to inflammatory challenges (A. N. Akopian et al., *Nat. Neurosci.* 1999; 2; 541-548) and that $Na_V1.8$ knockdown reduces pain behaviours, in this case neuropathic pain (J. Lai et al., *Pain,* 2002 (January); 95(1-2): 143-152). Coward et al. and Yiangou et al., have shown that $Na_V1.8$ appears to be expressed in pain conditions (*Pain.* 2000 (March); 85(1-2): 41-50 and FEBS Lett. 2000 (Feb. 11); 467(2-3): 249-252).

The $Na_V1.8$ channel has also been shown to be expressed in structures relating to the back and tooth pulp and there is evidence for a role in causalgia, inflammatory bowel conditions and multiple sclerosis (Bucknill et al., *Spine.* 2002 (Jan. 15); 27(2):135-140: Shembalker et al., *Eur J Pain.* 2001; 5(3): 319-323: Laird et al., *J Neurosci.* 2002 (Oct. 1); 22(19): 8352-8356: Black et al., *Neuroreport.* 1999 (Apr. 6); 10(5): 913-918 and *Proc. Natl. Acad. Sci. USA* 2000: 97: 11598-11602).

Examples of modulators of the $Na_V1.8$ sodium channel are disclosed in WO2008/135826 and WO2008/135830. There is, however, an ongoing need to provide new $Na_V1.8$ sodium channel inhibitors that are good drug candidates. These drug candidates should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as $Na_V1.8$ channel inhibitors. They should be non-toxic and demonstrate few side-effects. Ideal drug candidates should exist in a physical form that is stable, non-hygroscopic and easily formulated.

SUMMARY OF THE INVENTION

According to a first aspect of the invention there is provided a compound of formula (I)

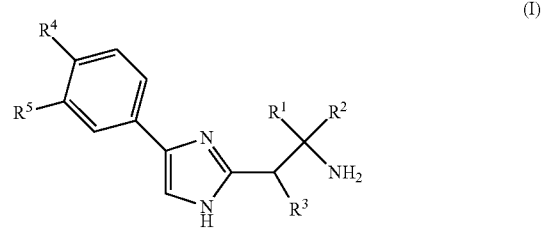

or a tautomer thereof, or a pharmaceutically acceptable salt of said compound or tautomer, wherein:

$R^1$ and $R^2$, together with the carbon to which they are attached, form a 4- to 7-membered ring, wherein:
  one member of said ring is O: and
  the remaining members of said ring are $CR^6R^7$, which may be the same or different at each occurrence;

$R^3$ is selected from the group consisting of H, $(C_1-C_3)$alkyl, cyclopropyl, cyclopropyl-$CH_2$—, —$CH_2OH$, —$CH_2OCH_3$, $(C_1-C_3)$fluoroalkyl, —OH, —$OCH_3$, F, —$NH_2$, $NHCH_3$, —$N(CH_3)_2$ and —$NHC(O)CH_3$;

$R^4$ is selected from the group consisting of —$CF_3$, —$OCF_3$, —$OCHF_2$, Cl and —$SF_5$;

$R^5$ is selected from the group consisting of H and —$CH_3$;

$R^6$ and $R^7$ are independently selected from the group consisting of H, —$CH_3$, —OH, —$OCH_3$, F, —$NH_2$, $NHCH_3$ and —$N(CH_3)_2$.

Described below are a number of embodiments (E) of this first aspect of the invention, where for convenience E1 is identical thereto.

E1 A compound of formula (I) as defined above, a tautomer thereof, or a pharmaceutically acceptable salt of said compound or said tautomer.

E2 A compound according to E1 wherein $R^1$ and $R^2$, together with the carbon to which they are attached, form a 4- to 7-membered ring of formula

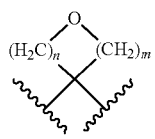

wherein m is 1, 2 or 3 and n is 1 or 2. Such a compound is represented by formula (Ia).

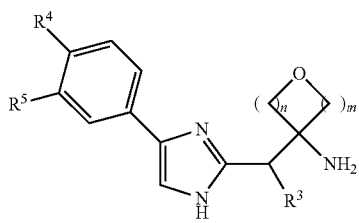

(Ia)

E3 A compound according to E2 wherein m is 1 and n is 1. Such a compound is represented by formula (Ib).

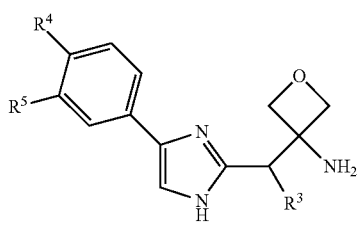

(Ib)

E4 A compound according to any of E1 to E3 wherein $R^3$ is selected from the group consisting of H, methyl, ethyl, n-propyl and isopropyl.

E5 A compound according to any of E1 to E4 wherein $R^5$ is H.

In a further aspect of the invention there is provided a compound according to formula (I) as described above for use as a medicament.

In a further aspect of the invention there is provided a compound according to formula (I) as described above for use in the treatment of pain.

In a further aspect of the invention there is provided a compound according to formula (I) as described above for use in the manufacture of a medicament for the treatment of pain.

In a further aspect of the invention there is provided a pharmaceutical composition comprising a compound according to formula (I) as described above and one or more pharmaceutically acceptable carriers.

In one embodiment, the pharmaceutical composition is adapted for topical administration.

In another embodiment, the pharmaceutical composition is adapted for intra-ocular administration.

In a further aspect of the invention there is provided a method for the treatment of a condition for which a $Na_V1.8$ modulator is indicated comprising the administration to a subject of a therapeutically effective amount of a compound according to formula (I) as described above.

In a further aspect of the invention there is provided a method for the treatment of pain in a subject in need of such treatment comprising the administration to said subject of a therapeutically effective amount of a compound according to formula (I) as described above.

DETAILED DESCRIPTION OF THE INVENTION

Alkyl groups, containing the requisite number of carbon atoms, can be unbranched or branched. $(C_1-C_3)$Alkyl includes methyl, ethyl, 1-propyl and 2-propyl.

Fluoroalkyl includes monofluoroalkyl, polyfluoroalkyl and perfluoroalkyl. Examples of $(C_1-C_3)$fluoroalkyl include fluoromethyl, difluoromethyl, trifluoromethyl, 2,2,2-trifluoroethyl, heptafluoro-n-propyl and 1,1,1,3,3,3-hexafluoro-2-propyl.

The compounds of formula (I) can exist in tautomeric forms. Specifically, the 2,4-disubstituted imidazole can exist as the (1H)-tautomer or the (3H)-tautomer. It will be understood that a 2,4-disubstituted-(3H)-imidazole may also be described as a 2,5-disubstituted-(1H)-imidazole.

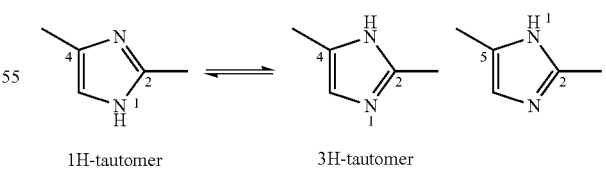

1H-tautomer      3H-tautomer

The compounds of formula (I) may exist in substantially pure (1H)-tautomeric form, substantially pure (3H)-tautomeric form, or as a mixture of tautomeric forms. All such tautomers and mixtures of tautomers are included within the scope of the present invention. References herein to specific compounds should be understood to refer to the compound and/or its tautomer.

Certain compounds of formula (I) include one or more stereogenic centers and so may exist as optical isomers, such as enantiomers and disastereomers. All such isomers and mixtures thereof are included within the scope of the present invention.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Hemisalts of acids and bases may also be formed, for example, hemisulphate salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by 0. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, $4^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the imidazole derivatives of the formula (I) can be prepared by the procedures described in the general methods presented below or by routine modifications thereof. The present invention also encompasses any one or more of these processes for preparing the imidazole derivatives of formula (I), in addition to any novel intermediates used therein.

In the following general methods, Ar represents

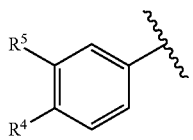

and $R^1$, $R^2$, $R^3$, $R^4$ and $R^5$ are as previously defined for an imidazole derivative of the formula (I) unless otherwise stated. In order to improve the legibility the schemes show structures wherein $R^6$ and $R^7$ are both H. Compounds wherein $R^6$ and/or $R^7$ are other than H may be prepared using analogous methods.

According to a first process, compounds of formula (I) may be prepared from compounds of formula (IV), as illustrated by Scheme 1.

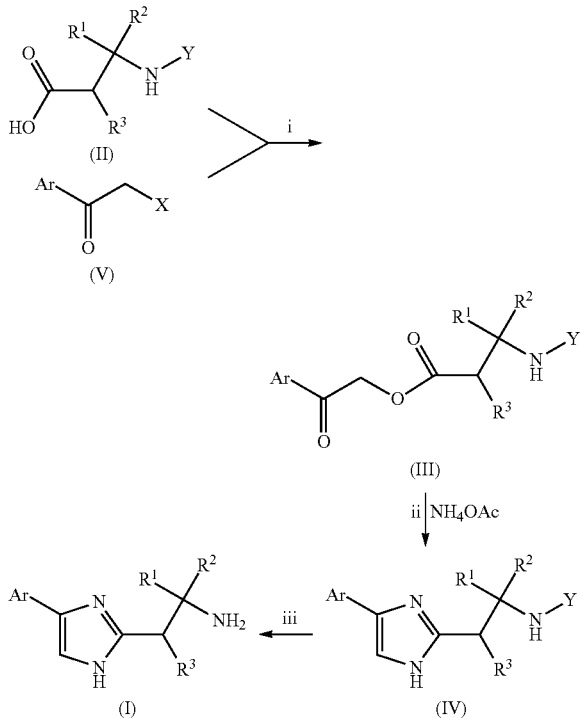

X is a suitable leaving group, typically Br.
Y is a suitable amine protecting group, typically tert-butoxycarbonyl, benzyloxycarbonyl or alkylsulfinyl Compounds of formula (II) are either commercially available or may be prepared according to the methods set out in Schemes 2 (for compounds wherein Y is tert-butoxycarbonyl or benzyloxycarbonyl) or 3 (for compounds wherein Y is alkylsulfinyl).

Compounds of formula (V) are either commercially available or may be prepared according to the methods set out in Scheme 4.

Compounds of formula (III) may be prepared from compounds of formula (II) according to process step (i), by alkylation with a compound of formula (V) in the presence of base in a suitable solvent. Typical conditions comprise combining an acid of formula (II) and an α-halo-ketone of formula (V) with an excess of base in a suitable solvent at a temperature between room temperature and 50° C. Preferred conditions comprise using 1.05 equivalents of α-bromo-ketone of formula (V) and 1.5 equivalents of caesium carbonate in acetonitrile at room temperature, or 1 equivalent of α-bromo-ketone of formula (V) and 1.5 equivalents of triethylamine in acetone at 50° C., or 1 equivalent of α-bromo-ketone of formula (V) and 1.5 equivalents of triethylamine in ethyl acetate at room temperature.

Compounds of formula (IV) can be prepared from compounds of formula (III) by process step (ii), a cyclisation reaction, in the presence of a suitable ammonium salt, typically ammonium acetate. Typical conditions comprise an excess of ammonium salt in a suitable organic solvent at a temperature between 100° C. and 130° C. Preferred conditions comprise 10 equivalents of ammonium acetate in anhydrous toluene at 100° C.-130° C.

Compounds of formula (I) can be prepared from compounds of formula (IV) by process step (iii), a deprotection reaction under hydrogenolysis or acidic conditions. Typical conditions are dependent on the nature of the protecting group. Where the protecting group is a tert-butoxycarbonyl group, conditions are acid mediated. Preferred conditions are an excess of HCl in 1,4-dioxane at room temperature. Where the protecting group is a benzyloxycarbonyl group, conditions are either acid mediated, typically using HBr in acetic acid at room temperature or by hydrogenolysis over a suitable hydrogenation catalyst, typically Pd/C or Pd(OH)$_2$/C.

According to a second process, compounds of formula (VI) (i.e. compounds of formula (II) wherein Y is tert-butyloxycarbonyl or benzyloxycarbonyl, $R^3$ is hydrogen and $R^1$ and $R^2$ together with the carbon atom to which they are attached form a 4- to 7-membered ring of formula

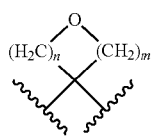

where m is 1, 2 or 3 and n is 1 or 2) may be prepared by the process illustrated by Scheme 2.

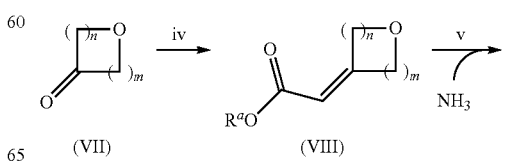

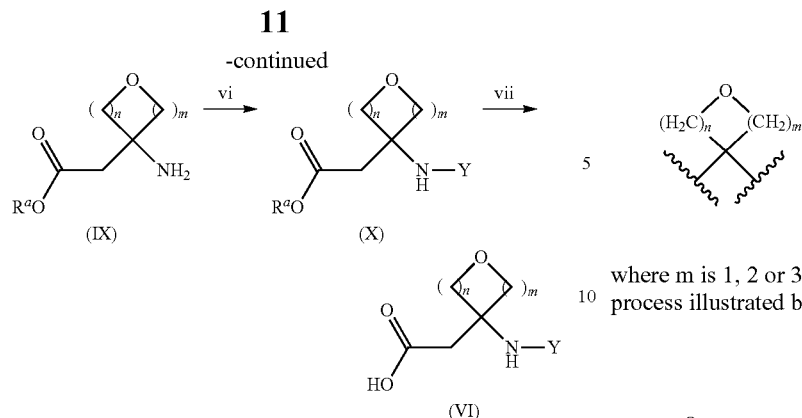

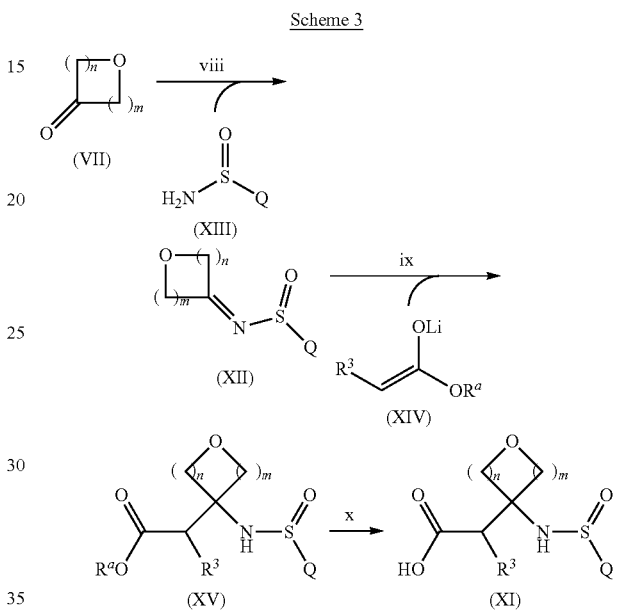

where m is 1, 2 or 3 and n is 1 or 2) may be prepared by the process illustrated by Scheme 3.

$R^a$ is a suitable alkyl protecting group, typically methyl or ethyl.

Y is tert-butyloxycarbonyl or benzyloxycarbonyl.

m is 1, 2 or 3, and n is 1 or 2.

Compounds of formula (VII) are commercially available or can be prepared using published methods.

Compounds of formula (VIII) can be prepared from compounds of formula (VII) by a Wittig-type reaction according to process step (iv), with a ketone of formula (VII) and either a phosphonate ester in the presence of a strong base or a phosphorane in a suitable solvent. In the case of the phosphonate ester, typical conditions comprise the phosphonate ester in the presence of a strong base in anhydrous THF at 0° C. Preferred conditions comprise triethyl phosphonoacetate with 1.1 equivalents of sodium hydride in anhydrous THF at 0° C. In the case of the phosphorane, preferred conditions comprise 1.01 equivalents of (carbethoxymethylene)triphenylphosphorane in dichloromethane at 0° C.

Compounds of formula (IX) can be prepared from compounds of formula (VIII) by process step (v), a conjugate addition reaction with a Michael acceptor of formula (VIII) and ammonia. Preferred conditions comprise an excess of ammonia in an alcoholic solvent at a temperature between 100° C. and 150° C. in a sealed vessel.

Compounds of formula (X) can be prepared from compounds of formula (IX) by process step (vi), a protection reaction of an amino ester of formula (IX). Typical conditions are dependent on the nature of the amine protecting group. Where the protecting group is a benzyloxycarbonyl group, typical conditions comprise benzylchloroformate in the presence of a base in a suitable solvent. Preferred conditions comprise 1.2 equivalents of benzylchloroformate and 3 equivalents of N,N-diisopropylethylamine in acetonitrile at room temperature, or 1.3 equivalents of benzylchloroformate and an aqueous solution of sodium carbonate in tert-butylmethyl ether at 5-20° C.

Compounds of formula (VI) can be prepared from compounds of formula (X) by process step (vii), a hydrolysis reaction of a protected amino ester of formula (X). Typical conditions comprise a base in a suitable solvent at a temperature between room temperature and 75° C. Preferred conditions comprise an aqueous solution of sodium hydroxide in methanol at 75° C. or an aqueous solution of sodium hydroxide in tert-butylmethylether at room temperature.

According to a third process, compounds of formula (XI) (i.e. compounds of formula (II) wherein Y is alkylsulfinyl and $R^1$ and $R^2$ together with the carbon atom to which they are attached form a 4- to 7-membered ring of formula $R^a$ is a suitable alkyl protecting group, typically methyl or ethyl.

Q is a suitable alkyl protecting group, typically tert-butyl.

m is 1, 2 or 3, and n is 1 or 2.

Compounds of formula (XIII) are commercially available.

Compounds of formula (XII) can be prepared from compounds of formula (VII) by an imine formation reaction according to process step (viii), with a ketone of formula (VII) and a sulfinamide of formula (XIII) in the presence of base in a suitable solvent. Preferred conditions comprise 1.0 equivalent of an alkyl sulfinamide (XIII) and 1.0 equivalent of caesium carbonate in dichloromethane at room temperature.

Compounds of formula (XV) can be prepared from compounds of formula (XII) by process step (ix), addition of a lithium enolate of formula (XIV) to a sulfinime of formula (XII). The lithium enolate is formed in situ from the appropriate ester in the presence of a lithium base in a suitable solvent at −78° C. Preferred conditions comprise of 2.1 equivalents of the appropriate ester and 2 equivalents of lithium diisopropylamine in anhydrous THF at −78° C., followed by addition of the sulfinimine of formula (XII).

Compounds of formula (XI) can be prepared from compounds of formula (XV) by process step (x), a hydrolysis reaction of the protected amino ester of formula (XIII). Typical conditions comprise a base in a suitable solvent at room temperature. Preferred conditions comprise an aqueous solution of sodium hydroxide in methanol.

According to a fourth process, compounds of formula (V) may be prepared using the methods illustrated in Scheme 4.

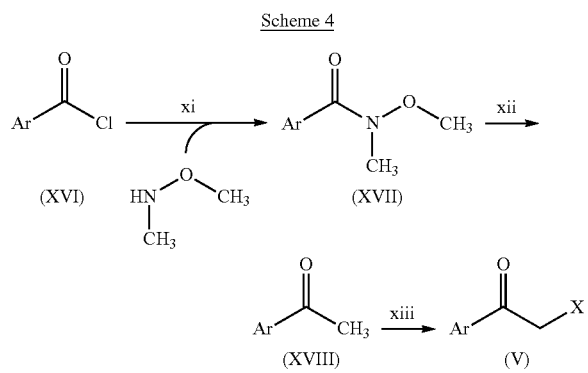

Compounds of formula (V) can be prepared from compounds of formula (XVIII) according to process step (xiii), a halogenation reaction. Preferred bromination (whereby X is Br) reaction conditions comprise a brominating agent, such as trimethylphenylammonium tribromide, in a suitable solvent at 0° C.

If non-commercial, compounds of formula (XVIII) can be prepared from compounds of formula (XVII) according to process step (xii), displacement of a Weinreb amide. Preferred conditions comprise methyl lithium in a suitable solvent at 0° C.

Compounds of formula (XVII) can be prepared from compounds of formula (XVI) according to process step (xi), an amide bond formation. Preferred conditions comprise O,N-dimethylhydroxylamine hydrochloride and suitable base, such as triethylamine in a suitable solvent at room temperature.

Referring to the general methods above, it will be readily understood to the skilled person that where protecting groups are present, these will be generally interchangeable with other protecting groups of a similar nature, e.g. where an amine is described as being protected with a tert-butoxycarbonyl group, this may be readily interchanged with any suitable amine protecting group. Suitable protecting groups are described in 'Protective Groups in Organic Synthesis' by T. Greene and P. Wuts ($3^{rd}$ edition, 1999, John Wiley and Sons).

The present invention also relates to novel intermediate compounds as defined above, all salts, solvates and complexes thereof and all solvates and complexes of salts thereof as defined hereinbefore for imidazole derivatives of formula (I). The invention includes all polymorphs of the aforementioned species and crystal habits thereof.

When preparing imidazole derivatives of formula (I) or amino acids of formula (VI) in accordance with the invention, it is open to a person skilled in the art to routinely select the best order of steps with which to synthesise the intermediates, and to choose the form of the intermediate compounds which provides the best combination of features for this purpose. Such features include the melting point, solubility, processability and yield of the intermediate form and the resulting ease with which the product may be purified on isolation.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, subcutaneous and trans-tympanic. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of formula (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., $Na_V1.8$ channel modulation. More particularly, the compounds of the invention are of use in the treatment of disorders for which a $Na_V1.8$ modulator is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a $Na_V1.8$ modulator is indicated.

In a further aspect of the invention there is provided use of a compound of the invention for the preparation of a medicament for the treatment of a disorder for which a $Na_V1.8$ modulator is indicated.

In a further aspect of the invention there is provided a method of treating a disorder in an animal (preferably a mammal, more preferably a human) for which a $Na_V1.8$ modulator is indicated, comprising administering to said animal a therapeutically effective amount of a compound of the invention.

Disorders for which a $Na_V1.8$ modulator is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56).

Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A $Na_V1.8$ modulator may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A $Na_V1.8$ modulator of formula (I), or a pharmaceutically acceptable salt thereof, as defined above, may be administered in combination with one or more agents selected from:
  an alternative $Na_V1.8$ modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
  an alternative sodium channel modulator, such as a $Na_V1.3$ modulator (e.g. as disclosed in WO2008/118758); or a $Na_V1.7$ channel modulator e.g. as disclosed in WO 2009/012242);
  an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
  a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);
  an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
  a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
  a barbiturate sedative, e.g. amobarbital, aprobarbital, butabarbital, butabital, mephobarbital, metharbital, methohexital, pentobarbital, phenobarbital, secobarbital, talbutal, theamylal or thiopental;
  a benzodiazepine having a sedative action, e.g. chlordiazepoxide, clorazepate, diazepam, flurazepam, lorazepam, oxazepam, temazepam or triazolam;
  an $H_1$ antagonist having a sedative action, e.g. diphenhydramine, pyrilamine, promethazine, chlorpheniramine or chlorcyclizine;
  a sedative such as glutethimide, meprobamate, methaqualone or dichloralphenazone;
  a skeletal muscle relaxant, e.g. baclofen, carisoprodol, chlorzoxazone, cyclobenzaprine, methocarbamol or orphrenadine;
  an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
  an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
  a tricyclic antidepressant, e.g. desipramine, imipramine, amitriptyline or nortriptyline;
  an anticonvulsant, e.g. carbamazepine, lamotrigine, topiratmate or valproate;
  a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
  a muscarinic antagonist, e.g. oxybutynin, tolterodine, propiverine, tropsium chloride, darifenacin, solifenacin, temiverine and ipratropium;
  a COX-2 selective inhibitor, e.g. celecoxib, rofecoxib, parecoxib, valdecoxib, deracoxib, etoricoxib, or lumiracoxib;
  a coal-tar analgesic, in particular paracetamol;
  a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
  a vanilloid receptor agonist (e.g. resinferatoxin) or antagonist (e.g. capsazepine);
  a beta-adrenergic such as propranolol;
  a local anaesthetic such as mexiletine;
  a corticosteroid such as dexamethasone;
  a 5-HT receptor agonist or antagonist, particularly a $5-HT_{1B/1D}$ agonist such as eletriptan, sumatriptan, naratriptan, zolmitriptan or rizatriptan;
  a $5-HT_{2A}$ receptor antagonist such as R(+)-alpha-(2,3-dimethoxy-phenyl)-1-[2-(4-fluorophenylethyl)]-4-piperidinemethanol (MDL-100907);
  a $5-HT_3$ antagonist, such as ondansetron
  a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
  Tramadol®;
  a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl- 3-azetidinyl)-2,6-dihydro-7H-pyrazolo[4,3-d] pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)-amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl) acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a $Na_v1.8$ modulator is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:
AcOH is acetic acid,
$Cs_2CO_3$ is caesium carbonate;
$Cu(acac)_2$ is copper (II) acetylacetonate;
CuI is copper (I) iodide;
$Cu(OAc)_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCl is 1-(3-dimethylaminopropyl)-3-ethylcarbodiimide hydrochloride;
EDTA is ethylenediaminetetraacetic acid;
ELSD is evaporative light scattering detection;
$Et_2O$ is diethyl ether;
EtOAc is ethyl acetate;
EtOH is ethanol;
HCl is hydrochloric acid;
IPA is isopropanol;
$Ir_2(OMe)_2COD_2$ is bis(1,5-cyclooctadiene)di-µ-methoxydi-iridium (I);
$K_2CO_3$ is potassium carbonate;
$KHSO_4$ is potassium hydrogen sulphate;
KOAc is potassium acetate;
KOH is potassium hydroxide;
$K_3PO_4$ is potassium phosphate tribasic;
LCMS is liquid chromatography mass spectrometry ($R_t$=retention time)
LiOH is lithium hydroxide;
MeOH is methanol;
$MgSO_4$ is magnesium sulphate;
NaH is sodium hydride;
$NaHCO_3$ is sodium hydrogencarbonate;
$Na_2CO_3$ is sodium carbonate;
$NaHSO_3$ is sodium bisulphite;
$NaHSO_4$ is sodium hydrogensulphate;
NaOH is sodium hydroxide;
$Na_2SO_4$ is sodium sulphate;
$NH_4Cl$ is ammonium chloride;
NMP is N-Methyl-2-pyrrolidone;
Pd/C is palladium on carbon;
$Pd(PPh_3)_4$ is palladium tetrakis(triphenylphosphine);
$Pd(dppf)_2Cl_2$ is [1,1'-bis(diphenylphosphino)ferrocene] dichloropalladium(II), complex with dichloromethane;
THF is tetrahydrofuran;
THP is tetrahydropyran;
TLC is thin layer chromatography; and
WSCDI is 1-(3-dimethylaminopropyl)-3-ethylcarbodiimide hydrochloride.

The invention is illustrated by the following representative Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (MS) were recorded using either electrospray ionisation (ESI) or atmospheric pressure chemical ionisation (APCI). The following abbreviations have been used for common solvents: $CDCl_3$, deuterochloroform; DMSO-$d_6$, deuterodimethylsulphoxide; $CD_3OD$, deuteromethanol; THF, tetrahydrofuran. LCMS indicates liquid chromatography mass spectrometry ($R_t$=retention time). Where ratios of solvents are given, the ratios are by volume.

Certain compounds of the Examples and Preparations were purified using Automated Preparative High Performance Liquid Chromatography (HPLC). Reversed-phase HPLC conditions were on FractionLynx systems. Samples were submitted dissolved in 1 mL of DMSO. Depending on the nature of the compounds and the results of a pre-analysis, the purification was performed under either acidic conditions ('A-HPLC') or basic conditions ('B-HPLC') at ambient temperature. Acidic runs were carried out on a Sunfire Prep C18 OBD column (19×100 mm, 5 µm), basic runs were carried out on an Xterra Prep MS C18 (19×100 mm, 5 µm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 30 v Capillary: 3.20 kv
ES– Cone voltage: –30 v Capillary: –3.00 kv
Desolvation gas: 600 L/hr
Source Temp: 120° C.
Scan range 150-900 Da The fraction collection was triggered by both MS and ELSD.

Quality control (QC) analysis was performed using a LCMS method. Acidic runs were carried out on a Sunfire C18 (4.6×50 mm, 5 µm), basic runs were carried out on a Xterra C18 (4.6×50 mm, 5 µm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 25 v Capillary: 3.30 kv
ES– Cone voltage: –30 v Capillary: –2.50 kv
Desolvation gas: 800 L/hr
Source Temp: 150° C.
Scan range 160-900 Da Unless carried out by Auto-HPLC (under conditions of A-HPLC or B-HPLC as just described, LCMS conditions were run according to one of the conditions given below (where ratios of solvents are given, the ratios are by volume):
6 Minute LC-MS Gradient and Instrument Conditions
Acid run: A: 0.1% formic acid in water B: 0.1% formic acid in acetonitrile Column: C18 phase Phenomenex Gemini 50×4.6 mm with 5 micron particle size. Gradient: 95-5% A over 3 min, 1 min hold, 1 ml/min. UV: 210 nm 450 nm DAD. Temperature: 50° C.

2 Minute LC-MS Gradient and Instrument Conditions

Acid run: A: 0.1% formic acid in water B: 0.1% formic acid in acetonitrile Column: $C_{18}$ phase Fortis Pace 20×2.1 mm with 3 micron particle size. Gradient: 70-2% A over 1.8 min, 0.2 min hold, 1.8 ml/min. UV: 210 nm 450 nm DAD. Temperature: 75° C.

C18 30 Minute Method LC-MS Gradient and Instrument Conditions

A: 0.1% formic acid in $H_2O$ B: 0.1% formic acid in MeCN Column: Phenomenex $C_{18}$ phase Gemini 150×4.6 mm with 5 micron particle size Gradient: 98-2% A over 18 min, 2 min hold, 1 ml/min. UV: 210 nm 450 nm DAD. Temperature: 50° C.

Phenyl Hexyl 30 Minute Method LC-MS Gradient and Instrument Conditions

A: 10 mM ammonium acetate in $H_2O$ B: 10 mM ammonium acetate in methanol Column: Phenomenex Phenyl Hexyl 150×4.6 mm with 5 micron particle size Gradient: 98-2% A over 18 min, 2 min hold, 1 ml/min. UV: 210 nm 450 nm DAD. Temperature: 50° C.

Unless otherwise noted, HPLC analysis conditions were run according to the conditions given below:

Ultra Acid Method HPLC Gradient and Instrument Conditions

HPLC analysis was performed using the ultra acid method. Zorbax SB-$C_{18}$ (3.0×50 mm, 1.8 μm), supplied by Crawford scientific at a column temperature of 50° C. A flow rate of 1.2 mL/min was used with mobile phase A: water+0.05% TFA (v/v) and B: acetonitrile. An Agilent 1100 LC pump ran a gradient elution from 5% to 100% B over 3.5 min followed by a 1 min hold at 100% B.

Example 1

3-({4-[4-(Trifluoromethoxy)phenyl]-1H-imidazol-2-yl}methyl)tetrahydro-2H-pyran-3-amine

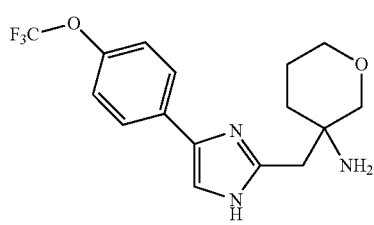 [SMILES: NC1(Cc2nc(-c3ccc(OC(F)(F)F)cc3)c[nH]2)CCCOC1]

Method A

To benzyl [3-({4-[4-(trifluoromethoxy)phenyl]-1H-imidazol-2-yl}methyl)tetrahydro-2H-pyran-3-yl]carbamate (Preparation 1, 0.120 g, 0.253 mmol) in acetic acid (1 mL) was added a solution of HBr in acetic acid (48%, 2 mL) and the reaction left to stir at room temperature for 1.5 hours before concentrating in vacuo. The residue was azeotroped with cyclohexane to yield an orange solid. The solid was purified by Isolute™ SCX ion exchange column eluting with methanol followed by 7M ammonia in methanol to afford a yellow oil. The oil was further purified by preparative HPLC conditions (B-HPLC) to afford the title compound.

LCMS (acidic QC method) Rt=2.16 min MS m/z 342 [MH]⁺

Example 2

3-{[4-(4-Chloro-3-methylphenyl)-1H-imidazol-2-yl]methyl}oxetan-3-amine

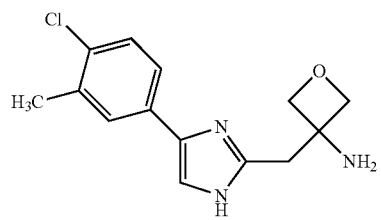 [SMILES: Cc1cc(-c2c[nH]c(CC3(N)COC3)n2)ccc1Cl]

Method B

Benzyl (3-{[4-(4-chloro-3-methylphenyl)-1H-imidazol-2-yl]methyl}oxetan-3-yl)carbamate (Preparation 3, 0.150 g, 0.364 mmol) was dissolved in methanol (5 mL) and hydrogenated at 50° C. through a 20% Pd(OH)₂ on carbon CAT-CART™ (30 mm) supplied by Thales Nanotechnology Inc® using the Thales Nanotechnology Inc® HC2 hydrogenater at a flow rate of 1 mL/min and a pressure of 1 Bar. The reaction was concentrated in vacuo. The residue was purified by preparative HPLC conditions (A-HPLC) to afford the title compound.

LCMS (acidic QC method) Rt=1.99 min MS m/z 278 [MH]⁺

The following examples 3 to 6 were prepared by methods analogous to Methods A and B as described for Examples 1 and 2 above. Unless otherwise noted, preparation details are as described for the method referred to.

Example 3

3-({4-[4-(Trifluoromethoxy)phenyl]-1H-imidazol-2-yl}methyl)tetrahydrofuran-3-amine

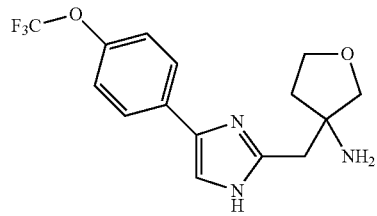 [SMILES: NC1(Cc2nc(-c3ccc(OC(F)(F)F)cc3)c[nH]2)CCOC1]

Prepared by Method A using benzyl [3-({4-[4-(trifluoromethoxy)phenyl]-1H-imidazol-2-yl}methyl)tetrahydrofuran-3-yl]carbamate (Preparation 2, 0.132 g, 0.286 mmol) but without the need for initial purification via Isolute™ SCX ion exchange column to afford the title compound.

LCMS (acidic QC method) Rt=2.23 min MS m/z 328 [MH]⁺

Example 4

3-({4-[4-(Trifluoromethyl)phenyl]-1H-imidazol-2-yl}methyl)oxetan-3-amine

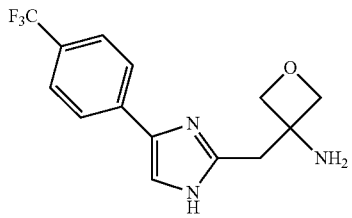 [SMILES: NC1(Cc2nc(-c3ccc(C(F)(F)F)cc3)c[nH]2)COC1]

Prepared by Method B using benzyl [3-({4-[4-(trifluoromethyl)phenyl]-1H-imidazol-2-yl}-methyl)oxetan-3-yl]carbamate (Preparation 5, 0.135 g, 0.310 mmol) to afford the title compound.
LCMS (acidic QC method) Rt=2.15 min MS m/z 298 [MH]⁺

Example 5

3-({4-[4-(Difluoromethoxy)phenyl]-1H-imidazol-2-yl}methyl)oxetan-3-amine

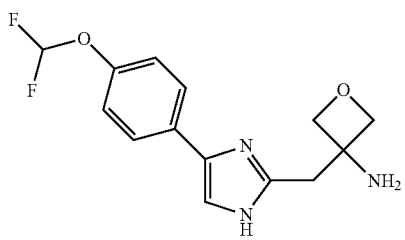 [SMILES: NC1(Cc2nc(-c3ccc(OC(F)F)cc3)c[nH]2)COC1]

Prepared by Method B using benzyl [3-({4-[4-(difluoromethoxy)phenyl]-1H-imidazol-2-yl}methyl)oxetan-3-yl]carbamate (Preparation 6, 0.133 g, 0.310 mmol). Purified by preparative HPLC conditions (B-HPLC) to afford the title compound.
LCMS (acidic QC method) Rt=2.30 min MS m/z 296 [MH]⁺

Example 6

3-({4-[4-(Pentafluoro-λ⁶-sulfanyl)phenyl]-1H-imidazol-2-yl}methyl)oxetan-3-amine

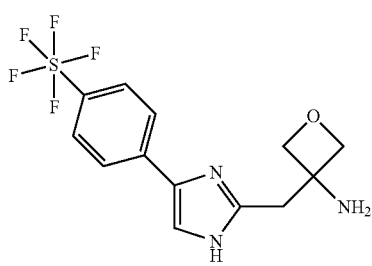 [SMILES: NC1(Cc2nc(-c3ccc(S(F)(F)(F)(F)F)cc3)c[nH]2)COC1]

Prepared by Method B using benzyl [3-({4-[4-(pentafluoro-λ⁶-sulfanyl)phenyl]-1H-imidazol-2-yl}methyl)oxetan-3-yl]carbamate (Preparation 7, 0.100 g, 0.204 mmol). Purified by preparative HPLC conditions (B-HPLC) to afford the title compound.
LCMS (acidic QC method) Rt=2.31 min MS m/z 356 [MH]+

Example 7

4-({4-[4-(Trifluoromethoxy)phenyl]-1H-imidazol-2-yl}methyl)tetrahydro-2H-pyran-4-amine

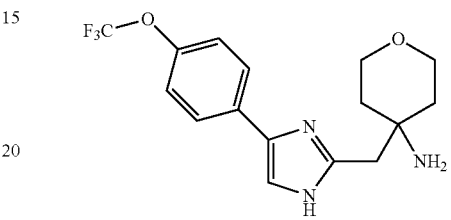

To tert-butyl [4-({4-[4-(trifluoromethoxy)phenyl]-1H-imidazol-2-yl}methyl)tetrahydro-2H-pyran-4-yl]carbamate (Preparation 4, 0.166 g, 0.376 mmol) was added 4M hydrogen chloride in 1,4-dioxane (3 mL) and the reaction left to stir at room temperature for 18 hours before concentrating in vacuo. The residue was purified by preparative HPLC conditions (A-HPLC) to afford the title compound.
LCMS (acidic QC method) Rt=1.98 min MS m/z 342 [MH]⁺

Example 8

3-({4-[4-(Trifluoromethoxy)phenyl]-1H-imidazol-2-yl}methyl)oxetan-3-amine

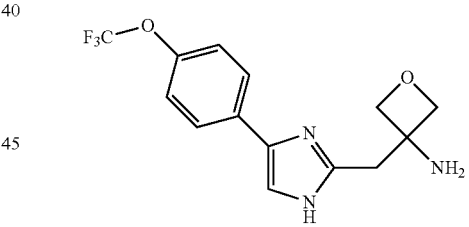

Benzyl [3-({4-[4-(trifluoromethoxy)phenyl]-1H-imidazol-2-yl}methyl)oxetan-3-yl]-carbamate (Preparation 11, 311 g, 695 mmol) was dissolved in methanol (3.2 L). 5% Palladium on carbon E105 R/W (EVONIK) (22 g, 7 wt %) was added and the reaction hydrogenated at 40° C., 100 psi for 18 hours. Hydrogen uptake was monitored and showed the reaction to be complete after 4 hours. The mixture was cooled to room temperature and filtered over Arbocel©. The filter cake was washed with methanol (2×1 L) and the filtrate concentrated in vacuo to afford a solid. The solid was dissolved in ethyl acetate (1 L) and filtered through a carbon tablet to remove traces of palladium. The solution was warmed to 50° C. and heptane (1 L) added. The solution was cooled slowly whereupon at 40° C. crystallisation was observed. The mixture was stirred at room temperature for 72 hours. The solid was collected by filtration and washed with ethyl acetate: heptane (1:1, 250 mL). The solid was dried in vacuo at 40° C. for 18 hours to afford the title compound as a crystalline solid.
HPLC (ultra acid method) Rt=1.996 min.

Example 9

3-(1-{4-[4-(Trifluoromethoxy)phenyl]-1H-imidazol-2-yl}ethyl)oxetan-3-amine

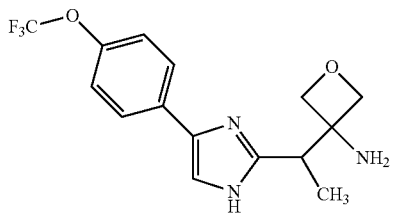 [SMILES: CC(c1nc(-c2ccc(OC(F)(F)F)cc2)c[nH]1)C1(N)COC1]

To a solution of 2-methyl-N-[3-(1-{4-[4-(trifluoromethoxy)phenyl]-1H-imidazol-2-yl}-ethyl)oxetan-3-yl]propane-2-sulfinamide (Preparation 9, 0.320 g, 0.74 mmol) in methanol (4 mL) at 0° C. was added 4M hydrogen chloride in 1,4-dioxane (4 mL) and the reaction left to stir for 2 hours. Solid sodium hydrogen carbonate was added to the reaction, followed by a saturated aqueous solution of sodium hydrogen carbonate. The mixture was extracted with dichloromethane. The organic layer was dried over $MgSO_4$ and concentrated in vacuo. The residue was purified by silica gel column chromatography to afford the title compound (0.243 g, 91% yield).

LCMS (2 min) Rt=0.96 min MS m/z 328 [MH]+

Examples 10 & 11

3-[(1S)-1-{4-[4-(Trifluoromethoxy)phenyl]-1H-imidazol-2-yl}ethyl]oxetan-3-amine and 3-[(1R)-1-{4-[4-(Trifluoromethoxy)phenyl]-1H-imidazol-2-yl}ethyl]oxetan-3-amine

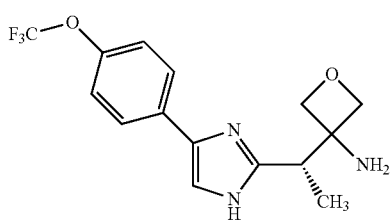

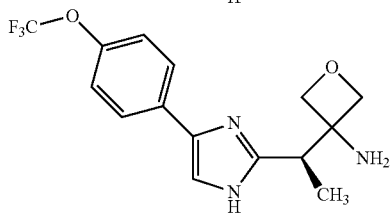

Racemic 3-(1-{4-[4-(trifluoromethoxy)phenyl]-1H-imidazol-2-yl}ethyl)oxetan-3-amine (Example 9, 0.243 g, 0.743 mmol) was dissolved in ethanol (1 mL). Enantiomers were separated by chiral preparative HPLC under basic conditions at ambient temperature on a Chiralpak AD-H column (250*, 20 mm i.d) supplied by Daicel Chemical Industries. A flow rate of 18 mL/min was used with mobile phase A: heptane and B: IPA+0.1% diethylamine (v/v). Two Agilent 1200 prep pumps supplied a mobile phase with a composition of 20% B. Run time was 10 minutes per 0.1 mL injection volume. Detection was achieved using an Agilent 1200 multiple wavelength UV absorbance detector set at 220 nm.

Enantiomer 1: Rt=5.89 min. >99.5% ee (58 mg, 24%)
Enantiomer 2: Rt=8.42 min. >99.5% ee (89 mg, 37%)
Enantiomer 1: $^1$HNMR (CDCl$_3$): δ 1.35 (d, 3H), 3.21 (s, 2H), 3.64 (q, 1H), 4.39 (d, 1H), 4.43 (d, 1H), 4.52 (d, 1H), 4.66 (d, 1H), 7.13-7.22 (m, 3H), 7.75 (br s, 2H).
Enantiomer 2: $^1$HNMR (CDCl$_3$): δ 1.35 (d, 3H), 3.21 (s, 2H), 3.64 (q, 1H), 4.39 (d, 1H), 4.43 (d, 1H), 4.52 (d, 1H), 4.66 (d, 1H), 7.13-7.22 (m, 3H), 7.75 (br s, 2H).

Example 12

3-(1-{4-[4-(Trifluoromethyl)phenyl]-1H-imidazol-2-yl}ethyl)oxetan-3-amine

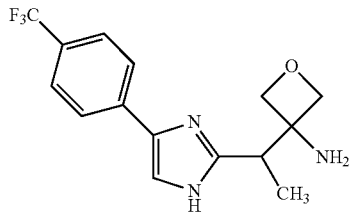 [SMILES: CC(c1nc(-c2ccc(C(F)(F)F)cc2)c[nH]1)C1(N)COC1]

Benzyl [3-(1-{4-[4-(trifluoromethyl)phenyl]-1H-imidazol-2-yl}ethyl)oxetan-3-yl]carbamate (Preparation 8, 0.95 g, 2.13 mmol) was dissolved in methanol (20 mL) and hydrogenated at room temperature and 100 psi. The reaction mixture was then filtered over Arbocel© and the resulting filtrate concentrated in vacuo. The residue was purified by silica gel column chromatography to afford the title compound as a solid (0.42 g, 63%).

LCMS (2 min) Rt=0.75 min. MS m/z 312 [MH$^+$], 310 [MH]$^-$

Examples 13 & 14

3-[(1S)-1-{4-[4-(Trifluoromethyl)phenyl]-1H-imidazol-2-yl}ethyl]oxetan-3-amine and 3-[(1R)-1-{4-[4-(Trifluoromethyl)phenyl]-1H-imidazol-2-yl}ethyl]oxetan-3-amine

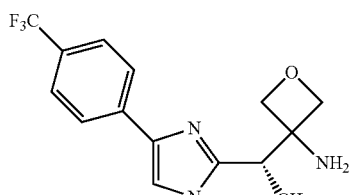

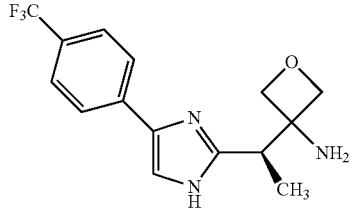

Racemic 3-(1-{4-[4-(trifluoromethyl)phenyl]-1H-imidazol-2-yl}ethyl)oxetan-3-amine (Example 12, 0.410 g, 1.32 mmol) was dissolved in ethanol (8.2 mL). Enantiomers were separated by chiral preparative HPLC under basic conditions at ambient temperature on a Chiralpak AD-H column (250*, 21.2 mm i.d) supplied by Daicel Chemical Industries. A flow rate of 18 mL/min was used with a mobile phase of: 70% heptane+30% IPA+0.3% diethylamine (v/v) supplied by an Agilent 1200 prep pump. An injection volume of 1 mL was used per run.

Detection was achieved using an Agilent 1200 multiple wavelength UV absorbance detector set at 220 nm and 254 nm.

Enantiomer 1: Rt=4.85 min. >99.5% ee (144 mg, 35%)

Enantiomer 2: Rt=5.89 min. >97.6% ee (142 mg, 35%)

Enantiomer 1: $^1$HNMR ($d_6$-DMSO): δ 1.25 (m, 3H), 3.35 (m, 1H), 4.23 (m, 1H), 4.30 (m, 1H), 4.43 (m, 2H), 7.63 (m, 3H), 7.90 (m, 2H).

Enantiomer 2: $^1$HNMR ($d_6$-DMSO): δ 1.25 (m, 3H), 3.35 (m, 1H), 4.23 (m, 1H), 4.30 (m, 1H), 4.43 (m, 2H), 7.63 (m, 3H), 7.90 (m, 2H).

Example 15

3-(1-{4-[4-(Trifluoromethoxy)phenyl]-1H-imidazol-2-yl}propyl)oxetan-3-amine

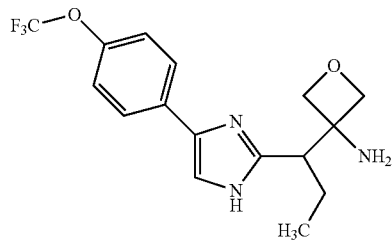 [SMILES: CCC(c1nc(-c2ccc(OC(F)(F)F)cc2)c[nH]1)C1(N)COC1]

To a solution of 2-methyl-N-[3-(1-{4-[4-(trifluoromethoxy)phenyl]-1H-imidazol-2-yl}-propyl)oxetan-3-yl]propane-2-sulfinamide (Preparation 10, 0.450 g, 1.01 mmol) in methanol (5 mL) at 0° C. was added 4M hydrogen chloride in 1,4-dioxane (1 mL) and the reaction left to stir for 4 hours. Solid sodium hydrogen carbonate was added to the reaction, followed by a saturated aqueous solution of sodium hydrogen carbonate. The mixture was extracted with dichloromethane. The organic layer was dried over MgSO$_4$ and concentrated in vacuo. The residue was purified by silica gel column chromatography to afford the title compound (0.154 g, 45% yield).

$^1$HNMR (CDCl$_3$): δ 1.0 (t, 3H), 1.65 (m, 2H), 3.4 (m, 1H), 4.25 (d, 1H), 4.45 (m, 2H), 4.75 (d, 1H), 7.2-7.3 (m, 4H), 7.75 (d, 2H).

LCMS (2 min) Rt=1.57 min MS m/z 342 [MH]$^+$, 340 [MH]$^-$

Examples 16 & 17

3-((1S)-1-{4-[4-(Trifluoromethoxy)phenyl]-1H-imidazol-2-yl}propyl)oxetan-3-amine and 3-((1R)-1-{4-[4-(Trifluoromethoxy)phenyl]-1H-imidazol-2-yl}propyl)oxetan-3-amine

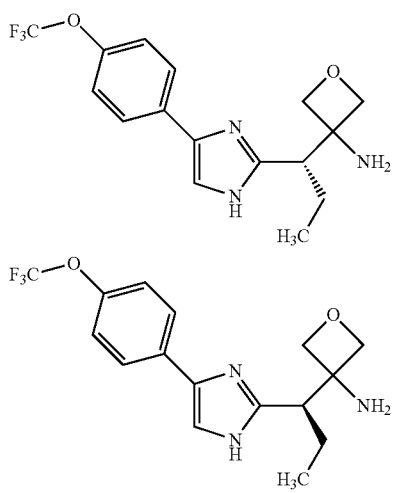

Racemic 3-(1-{4-[4-(trifluoromethoxy)phenyl]-1H-imidazol-2-yl}propyl)oxetan-3-amine (Example 15, 0.145 g, 1.01 mmol) was dissolved in a mixture of 70% heptane and 30% IPA (3 mL). Enantiomers were separated by chiral preparative HPLC under basic conditions at ambient temperature on a Chiralpak AD-H column (250*, 20 mm i.d) supplied by Daicel Chemical Industries. A flow rate of 1 mL/min was used with a mobile phase of: 90% heptane+10% IPA+0.1% diethylamine (v/v) delivered by a Waters 515 HPLC prep pump over a 20 minute run time. Detection was achieved using an Agilent 119 UV absorbance detector (UV), followed in series by a Polymer Labs PL-ELS 2100 detector (ELSD) and a Waters ZQ micromass mass spectrometer (MS).

Enantiomer 1: Rt=7.95 min. MS m/z 342 [MH]$^+$

Enantiomer 2: Rt=10.39 min. MS m/z 342 [MH]$^+$

QC analysis was performed under basic conditions at ambient temperature on a Chiralpak AD-H column (250*, 10 mm i.d) supplied by Daicel Chemical Industries. A flow rate of 1 mL/min was used with a mobile phase of: 80% heptane+20% IPA+0.2% diethylamine (v/v) over a 10 minute run time. Detection was achieved using an Agilent 100 detector (DAD), followed in series by a Polymer Labs PL-ELS 2100 detector (ELSD) and a Waters ZQ micromass mass spectrometer (MS).

Enantiomer 1: Rt=4.58 min. MS m/z 342 [MH]$^+$ >99/5% ee

Enantiomer 2: Rt=5.26 min. MS m/z 342 [MH]$^+$ >99/5% ee

Preparation 1

Benzyl [3-({4-[4-(trifluoromethoxy)phenyl]-1H-imidazol-2-yl}methyl)tetrahydro-2H-pyran-3-yl]carbamate Method C Ammonium acetate (1.58 g, 20.5 mmol) was suspended in anhydrous toluene (10 mL) and heated to 100° C. until fully solubilised. A solution of 2-oxo-2-[4-(trifluoromethoxy)phenyl]ethyl (3-{[(benzyloxy)carbonyl]amino}tetrahydro-2H-pyran-3-yl)acetate (Preparation 20, 1.11 g, 2.046 mmol) in anhydrous toluene (10 mL) was added to the reaction. The temperature was increased to 120° C. and the reaction refluxed for 2.5 hours. Once cooled, the reaction was partitioned between dichloromethane (3×5 mL) and water (5 mL). The organic layer was separated by phase separation cartridge and concentrated in vacuo to give an oil. The oil was purified by silica gel column chromatography (0-50% ethyl acetate in heptane gradient elution) to afford the title compound as a yellow oil (0.48 g, 49% yield).

$^1$HNMR (CDCl$_3$): δ 1.45 (m, 2H), 1.7 (m, 1H), 2.2 (m, 1H), 2.85 (d, 1H), 3.35 (m, 3H), 3.75 (m, 1H), 3.85 (m, 1H), 4.95 (d, 2H), 5.05 (d, 1H), 6.85 (br s, 1H), 7.1 (d, 2H), 7.3 (m, 5H), 7.6 (br m, 2H).

LCMS (2 min) Rt=1.30 min MS m/z 476 [MH]$^+$, 474 [MH]$^-$

Preparation 2

Benzyl [3-({4-[4-(trifluoromethoxy)phenyl]-1H-imidazol-2-yl}methyl)tetrahydrofuran-3-yl]carbamate Method D 2-Oxo-2-[4-(trifluoromethoxy)phenyl]ethyl (3-{[(benzyloxy)carbonyl]amino}-tetrahydrofuran-3-yl)acetate (Preparation 13, 0.634 g, 1.317 mmol), ammonium acetate (1.9 g, 25 mmol) and molecular sieves (3 Å) were suspended in anhydrous toluene (5 mL) and heated to 110° C. for 18 hours. Once cooled the reaction was partitioned between dichloromethane (3×5 mL) and water (5 mL) The organic layer was separated by phase separation cartridge and concentrated in vacuo to give an oil. The reaction had not gone to completion by 2 min LCMS analysis, therefore the oil, ammonium acetate (1.5 g, 19 mmol) and molecular sieves (3 Å) were placed in a microwave vial with anhydrous toluene (5 mL) and heated at 150° C. for 1 hour in a Biotage Initiator™ microwave. Once cooled the reaction was partitioned between dichloromethane (3×5 mL) and water (5 mL) The organic layer was separated by phase separation cartridge and concentrated in vacuo to give an oil. The oil was purified by silica gel column chromatography (0-100% ethyl acetate in heptane gradient elution) to afford the title compound as a yellow oil (0.132 g, 22% yield).

LCMS (2 min) Rt=1.30 min MS m/z 462 [MH]$^+$, 460 [MH]$^-$

The following Preparations 3 to 8 were prepared by methods analogous to Methods C and D as described for Preparations 1 and 2 above. Unless otherwise noted, preparation details are as described for the method referred to.

Preparation 3

Benzyl (3-{[4-(4-chloro-3-methylphenyl)-1H-imidazol-2-yl]methyl}oxetan-3-yl)carbamate Prepared by Method C using 2-(4-chloro-3-methylphenyl)-2-oxoethyl (3-{[(benzyloxy)-carbonyl]amino}oxetan-3-yl)acetate (Preparation 12, 0.488 g, 1.13 mmol). The mixture was partitioned between ethyl acetate and water. The organic layer was dried over MgSO$_4$ and concentrated in vacuo. The residue was purified by silica gel column chromatography to afford the title compound (0.297 g, 64% yield).

LCMS (2 min) Rt=1.25 min MS m/z 412 [MH]+

Preparation 4 tert-Butyl [4-({4-[4-(trifluoromethoxy)phenyl]-1H-imidazol-2-yl}methyl)tetrahydro-2H-pyran-4-yl]carbamate Prepared by Method D using 2-oxo-2-[4-(trifluoromethoxy)phenyl]ethyl {4-[(tert-butoxycarbonyl)amino]tetrahydro-2H-pyran-4-yl}acetate (Preparation 19, 0.485 g, 1.051 mmol). The residue was purified by silica gel column chromatography (0-100% ethyl acetate+3% triethylamine (v/v) in heptane gradient elution) to afford the title compound as a yellow oil (0.166 g, 36% yield).

LCMS (2 min) Rt=1.25 min MS m/z 442 [MH]$^+$, 440 [MH]$^-$

Preparation 5

Benzyl [3-({4-[4-(trifluoromethyl)phenyl]-1H-imidazol-2-yl}methyl)oxetan-3-yl]carbamate Prepared by Method C using 2-oxo-2-[4-(trifluoromethyl)phenyl]ethyl (3-{[(benzyloxy)-carbonyl]amino}oxetan-3-yl)acetate (Preparation 14, 0.510 g, 1.13 mmol). The mixture was partitioned between ethyl acetate and water. The organic layer was dried over MgSO$_4$ and concentrated in vacuo. The residue was purified by silica gel column chromatography to afford the title compound (0.273 g, 56% yield).

LCMS (2 min) Rt=1.32 min MS m/z 432 [MH]$^+$

Preparation 6

Benzyl [3-({4-[4-(difluoromethoxy)phenyl]-1H-imidazol-2-yl}methyl)oxetan-3-yl]carbamate Prepared by Method C using 2-[4-(difluoromethoxy)phenyl]-2-oxoethyl (3-{[(benzyloxy)-carbonyl]amino}oxetan-3-yl)acetate (Preparation 15, 0.508 g, 1.13 mmol). The mixture was partitioned between ethyl acetate and water. The organic layer was dried over MgSO$_4$ and concentrated in vacuo. The residue was purified by silica gel column chromatography to afford the title compound (0.269 g, 56% yield).

LCMS (2 min) Rt=1.13 min MS m/z 430 [MH]$^+$

Preparation 7

Benzyl [3-({4-[4-(pentafluoro-λ$^6$-sulfanyl)phenyl]-1H-imidazol-2-yl}methyl)oxetan-3-yl]carbamate Prepared by Method C using 2-oxo-2-[4-(pentafluoro-λ$^6$-sulfanyl)phenyl]ethyl (3-{[(benzyloxy)carbonyl]amino}oxetan-3-yl)acetate (Preparation 18, 0.9 g, 1.77 mmol). The reaction was refluxed for 18 hours. The mixture was partitioned between ethyl acetate and water. The organic layer was dried over MgSO$_4$ and concentrated in vacuo. The residue was purified by silica gel column chromatography to afford the title compound (0.227 g, 26% yield).

$^1$HNMR (CDCl$_3$): δ 3.50 (s, 2H), 4.70 (d, 2H), 4.85 (d, 2H), 5.10 (s, 2H), 5.80 (br s, 1H), 7.3-7.45 (m, 8H), 7.65-7.8 (m, 3H).

Preparation 8

Benzyl [3-(1-{4-[4-(trifluoromethyl)phenyl]-1H-imidazol-2-yl}ethyl)oxetan-3-yl]carbamate Prepared by Method C using 2-oxo-2-[4-(trifluoromethyl)phenyl]ethyl 2-(3-{[(benzyloxy)-carbonyl]amino}oxetan-3-yl)propanoate (Preparation 22, 2.15 g, 4.62 mmol). The reaction was refluxed for 12 hours. The mixture was partitioned between ethyl acetate and water. The organic layer was dried over $MgSO_4$ and concentrated in vacuo. The residue was purified by silica gel column chromatography to afford the title compound (0.983 g, 48% yield).

LCMS (2 min) Rt=0.97 min. MS m/z 446 [MH]$^+$, 444 [MH]$^-$

Preparation 9

2-Methyl-N-[3-(1-{4-[4-(trifluoromethoxy)phenyl]-1H-imidazol-2-yl}ethyl)oxetan-3-yl]propane-2-sulfinamide 2-Oxo-2-[4-(trifluoromethoxy)phenyl]ethyl 2-{3-[(tert-butylsulfinyl)amino]oxetan-3-yl}-propanoate (Preparation 16, 1.4 g, 3.10 mmol) and ammonium acetate (2.44 g, 31.0 mmol) were refluxed in toluene (40 mL) at 130° C. for 18 hours. Once cooled, water was added and the mixture extracted with ethyl acetate. The organic layer was dried over $MgSO_4$ then concentrated in vacuo. The residue was purified by silica gel column chromatography to afford the title compound (0.323 g, 24% yield).

LCMS (2 min) Rt=1.40 min MS m/z 432 [MH]$^+$, 430 [MH]$^-$

Preparation 10

2-Methyl-N-[3-(1-{4-[4-(trifluoromethoxy)phenyl]-1H-imidazol-2-yl}propyl)oxetan-3-yl]propane-2-sulfinamide 2-Oxo-2-[4-(trifluoromethoxy)phenyl]ethyl 2-{3-[(tert-butylsulfinyl)amino]oxetan-3-yl}-butanoate (Preparation 17, 3.4 g, 7.3 mmol) and ammonium acetate (5.74 g, 73.0 mmol) were refluxed in toluene (40 mL) at 130° C. for 18 hours. Once cooled, water was added and the mixture extracted with ethyl acetate. The organic layer was dried over $MgSO_4$ then concentrated in vacuo. The residue was purified by silica gel column chromatography to afford the title compound (2.527 g, 78% yield).

LCMS (2 min) Rt=1.52 min MS m/z 446 [MH]$^+$, 444 [MH]$^-$

LCMS (6 min acidic) Rt=2.30 min MS m/z 446 [MH]$^+$, 444 [MH]$^-$

Preparation 11

Benzyl [3-({4-[4-(trifluoromethoxy)phenyl]-1H-imidazol-2-yl}methyl)oxetan-3-yl]carbamate Ammonium acetate (1.22 Kg, 15 mol) was stirred in toluene (12 L) and heated to 100° C. for 30 minutes until the solid had melted. A solution of 2-oxo-2-[4-(trifluoromethoxy)-phenyl]ethyl (3-{[(benzyloxy)carbonyl]amino}oxetan-3-yl)acetate (Preparation 21, 700 g, 1.5 mol) in toluene (2 L) was added rapidly and the temperature increased to 130° C. and heated at vigorous reflux for 4 hours. The reaction was cooled to room temperature, water (4 L) added and the mixture stirred for 10 minutes before leaving to stand for 2 hours. The organic layer was separated and concentrated in vacuo to afford a thick orange oil. Dichloromethane (5 L) was added and the solution gently agitated by turning slowly on the rotary for 72 hours. A white precipitate was then observed. The solution volume was reduced in vacuo to 1 L and the mixture filtered through Arbocel©. The gelatinous solid was washed with dichloromethane (2 L) and the filtrate concentrated in vacuo to afford a dark orange mobile oil. The oil was purified by silica gel column chromatography eluting with tert-butyl methyl ether to afford the title compound as a light orange oil (311 g, 46% yield).

HPLC (ultra acid method) Rt=2.532 min.

Preparation 12

2-(4-Chloro-3-methylphenyl)-2-oxoethyl (3-{[(benzyloxy)carbonyl]amino}oxetan-3-yl)acetate Method E (3-{[(Benzyloxy)carbonyl]amino}oxetan-3-yl)acetic acid (Preparation 25, 0.3 g, 1.13 mmol), 2-bromo-1-(4-chloro-3-methylphenyl)ethanone (0.294 g, 1.19 mmol) and cesium carbonate (0.553 g, 1.70 mmol) were stirred in acetonitrile (10 mL) at room temperature for 2 hours. The reaction was concentrated in vacuo and partitioned between ethyl acetate and water. The organic layer was dried over $MgSO_4$ and concentrated in vacuo to afford the title compound which was used without purification in the next step.

LCMS (2 min) Rt=1.70 min MS m/z 432 [MH]$^+$, 454 [MNa]$^+$, 430 [MH]$^-$

Preparation 13

2-Oxo-2-[4-(trifluoromethoxy)phenyl]ethyl (3-{[(benzyloxy)carbonyl]amino}-tetrahydrofuran-3-yl)acetate Method F (3-{[(Benzyloxy)carbonyl]amino}tetrahydrofuran-3-yl)acetic acid (Preparation 24, 0.311 g, 1.11 mmol) and triethylamine (0.233 mL, 1.67 mmol) were stirred in acetone (4 mL). A solution of 2-bromo-1-[4-(trifluoromethoxy)phenyl]ethanone (0.315 g, 1.11 mmol) in acetone (4 mL) was added and the reaction heated to 50° C. for 1 hour. Rapid formation of a white precipitate was observed. The reaction was partitioned between dichloromethane and water. The organic layer was separated by phase separation cartridge and concentrated in vacuo to afford the title compound as an oil which was used without purification in the next step (0.634 g, 118% yield).

LCMS (2 min) Rt=1.73 min MS m/z 482 [MH]$^+$, 504 [MNa]$^+$, 480 [MH]$^-$

The following Preparations 14 to 20 were prepared by methods analogous to Methods E and F as described for Preparations 12 and 13 above. Unless otherwise noted, preparation details are as described for the method referred to.

Preparation 14

2-Oxo-2-[4-(trifluoromethyl)phenyl]ethyl (3-{[(benzyloxy)carbonyl]amino}oxetan-3-yl)acetate Prepared by Method E using (3-{[(benzyloxy)carbonyl]amino}oxetan-3-yl)acetic acid (Preparation 25, 0.3 g, 1.13 mmol) and 2-bromo-1-[4-(trifluoromethyl)phenyl]ethanone (0.317 g, 1.19 mmol) to afford the title compound.

LCMS (2 min) Rt=1.68 min MS m/z 452 [MH]$^+$, 474 [MNa]$^+$, 450 [MH]$^-$

Preparation 15

2-[4-(Difluoromethoxy)phenyl]-2-oxoethyl (3-{[(benzyloxy)carbonyl]amino}oxetan-3-yl)acetate Prepared by Method E using (3-{[(benzyloxy)carbonyl] amino}oxetan-3-yl)acetic acid (Preparation 25, 0.3 g, 1.13 mmol) and 2-bromo-1-[4-(difluoromethoxy)phenyl]ethanone (0.315 g, 1.19 mmol) to afford the title compound.

LCMS (2 min) Rt=1.63 min MS m/z 472 [MNa]$^+$, 448 [MH]$^-$

Preparation 16

2-Oxo-2-[4-(trifluoromethoxy)phenyl]ethyl 2-{3-[(tert-butylsulfinyl)amino]oxetan-3-yl}propanoate Prepared by Method E using 2-{3-[(tert-butylsulfinyl) amino]oxetan-3-yl}propanoic acid (Preparation 26, 1.18 g, 4.733 mmol) and 2-bromo-1-[4-(trifluoromethoxy)phenyl]-ethanone (1.47 g, 5.21 mmol). The residue was purified by silica gel column chromatography to afford the title compound (1.413 g, 66% yield).

LCMS (2 min) Rt=1.65 min MS m/z 452 [MH]$^+$, 474 [MNa]$^+$, 450 [MH]$^-$

Preparation 17

2-Oxo-2-[4-(trifluoromethoxy)phenyl]ethyl 2-{3-[(tert-butylsulfinyl)amino]oxetan-3-yl}butanoate Prepared by Method E using 2-{3-[(tert-butylsulfinyl) amino]oxetan-3-yl}butanoic acid (Preparation 27, 2.658 g, 10.1 mmol) and 2-bromo-1-[4-(trifluoromethoxy)phenyl]-ethanone (3.14 g, 11.1 mmol). The reaction was stirred at room temperature for 3 hours. The residue was purified by silica gel column chromatography to afford the title compound (3.435 g, 73% yield).

LCMS (2 min) Rt=1.68 min MS m/z 466 [MH]$^+$, 464 [MH]$^-$

Preparation 18

2-Oxo-2-[4-(pentafluoro-$\lambda^6$-sulfanyl)phenyl]ethyl (3-{[(benzyloxy)carbonyl]amino}oxetan-3-yl)acetate Prepared by Method E using (3-{[(benzyloxy)carbonyl] amino}oxetan-3-yl)acetic acid (Preparation 25, 0.647 g, 2.44 mmol) and 2-bromo-1-[4-(pentafluoro-$\lambda^6$-sulfanyl)phenyl]-ethanone (Preparation 40, 0.793 g, 2.44 mmol) to afford the title compound.

LCMS (2 min) Rt=1.74 min MS m/z 510 [MH]$^+$, 532 [MNa]$^+$

Preparation 19

2-Oxo-2-[4-(trifluoromethoxy)phenyl]ethyl {4-[(tert-butoxycarbonyl)amino]tetrahydro-2H-pyran-4-yl}acetate Prepared by Method F using {4-[(tert-butoxycarbonyl) amino]tetrahydro-2H-pyran-4-yl}acetic acid (0.259 g, 1.00 mmol) and 2-bromo-1-[4-(trifluoromethoxy)phenyl]-ethanone (0.283 g, 1.00 mmol). The reaction was stirred at 50° C. for 50 minutes. The residue was isolated as a crude oil that crystallised to afford the title compound as a solid (0.485 g, 105% yield).

LCMS (2 min) Rt=1.73 min MS m/z 484 [MNa]$^+$, 460 [MH]$^-$

Preparation 20

2-Oxo-2-[4-(trifluoromethoxy)phenyl]ethyl (3-{[(benzyloxy)carbonyl]amino}tetrahydro-2H-pyran-3-yl)acetate Prepared by Method F using (3-{[(benzyloxy)carbonyl] amino}tetrahydro-2H-pyran-3-yl)-acetic acid (Preparation 23, 0.6 g, 2.05 mmol) and 2-bromo-1-[4-(trifluoromethoxy)-phenyl]ethanone (0.579 g, 0.205 mmol). The reaction was stirred at 50° C. for 1.5 hours.

LCMS (2 min) Rt=1.75 min MS m/z 496, [MH]$^+$, 518 [MNa]$^+$, 494 [MH]$^-$

Preparation 21

2-Oxo-2-[4-(trifluoromethoxy)phenyl]ethyl (3-{[(benzyloxy)carbonyl]amino}oxetan-3-yl)acetate (3-{[(Benzyloxy)carbonyl]amino}oxetan-3-yl)acetic acid (Preparation 25, 1.011 Kg, 3.812 mol) was stirred in ethyl acetate (8 L). 2-Bromo-1-[4-(trifluoromethoxy)phenyl]-ethanone (1.08 Kg, 3.81 mol) was added, followed by triethylamine (585 mL, 4.19 mol). The reaction was initially fully solubilised, but a precipitate was then observed. The reaction was washed with water (2×4 L), then concentrated in vacuo to afford the title compound as a mobile orange oil (1.903 Kg, 107%, contains residual ethyl acetate).

HPLC (ultra acid method) Rt=3.290 min.

Preparation 22

2-Oxo-2-[4-(trifluoromethyl)phenyl]ethyl 2-(3-{[(benzyloxy)carbonyl]amino}oxetan-3-yl)propanoate 2-(3-{[(Benzyloxy)carbonyl]amino}oxetan-3-yl)propanoic acid (Preparation 28, 1.5 g, 5.37 mmol) and triethylamine (1.12 mL, 8.06 mmol) were stirred in ethyl acetate (50 mL). 2-Bromo-1-[4-(trifluoromethyl)phenyl]ethanone (1.51 g, 5.64 mmol) was added and the reaction was stirred at room temperature overnight. The reaction mixture was diluted with ethyl acetate and washed with brine. The organic layer was separated, dried over anhydrous magnesium sulphate, filtered and concentrated in vacuo. The residue was purified by silica gel column chromatography to afford the title compound as an oil (2.19 g, 88%).

$^1$HNMR (CDCl$_3$): δ 1.43 (m, 3H), 3.40 (m, 1H), 4.70 (m, 2H), 4.80 (m, 1H), 4.90 (m, 1H), 5.10 (m, 2H), 5.35 (m, 2H), 6.05 (br s, 1H), 7.35 (m, 5H), 7.80 (m, 2H), 8.00 (m, 2H).

Preparation 23

(3-{[(Benzyloxy)carbonyl]amino}tetrahydro-2H-pyran-3-yl)acetic acid

Method G

Ethyl (3-aminotetrahydro-2H-pyran-3-yl)acetate (Preparation 32, 1.33 g, 7.109 mmol), benzyl chloroformate (1.53 g, 8.53 mmol) and N,N-diisopropylethylamine (3.72 mL, 21.3 mmol) were stirred in anhydrous acetonitrile (30 mL) for 18 hours at room temperature. The reaction was concentrated in vacuo then partitioned between ethyl acetate and water. The organic layer was dried over MgSO$_4$ and concentrated in vacuo. The residue was purified by silica gel column chromatography eluting with heptane:ethyl acetate:methanol (100:0:0-0:90:10). The oil isolated was then dissolved in methanol (10 mL) and a 1M aqueous solution of sodium hydroxide (10 mL) and heated to 75° C. for 18 hours. The methanol was removed in vacuo and the mixture partitioned between dichloromethane (10 mL) and water. The aqueous layer was acidified with 2M aqueous hydrogen chloride and extracted with dichloromethane (4×10 mL). The organic layer was dried over MgSO$_4$ to afford the title compound as a oil (0.6 g, 29% yield over 2 steps).

$^1$HNMR (CDCl$_3$): δ 1.5-1.6 (m, 1H), 1.6-1.7 (m, 1H), 1.7-1.8 (m, 1H), 2.3 (m, 1H), 2.7 (br m, 1H), 3.0 (br m, 1H), 3.5-3.6 (m, 2H), 3.8 (m, 1H), 3.9 (d, 1H), 5.1 (s, 2H), 7.35-7.40 (m, 5H).

LCMS (2 min) Rt=1.34 min MS m/z 292 [MH]$^-$, 316 [MNa]$^+$

The following Preparation 24 was prepared by a method analogous to Method G as described for Preparation 23 above. Unless otherwise noted, preparation details are as described for the method referred to.

Preparation 24

(3-{[(Benzyloxy)carbonyl]amino}tetrahydrofuran-3-yl)acetic acid

Prepared by Method G using ethyl (3-aminotetrahydrofuran-3-yl)acetate (Preparation 31, 1.43 g, 8.25 mmol) to afford the title compound as an oil (0.311 g, 14% yield over 2 steps).

LCMS (2 min) Rt=1.26 min MS m/z 278 [MH]$^-$, 302 [MNa]$^+$

Preparation 25

(3-{[(Benzyloxy)carbonyl]amino}oxetan-3-yl)acetic acid tert-Butyl methyl ether (2.5 L) and an aqueous solution of sodium carbonate (750 g in 2.2 L water, 7.07 mol) were stirred. Ethyl (3-aminooxetan-3-yl)acetate (Preparation 30, 875 g, 5.5 mol) was added to the reaction followed by further tert-butyl methyl ether (2.5 L). The reaction was cooled to 5° C. and benzyl chloroformate (1.21 Kg, 7.09 mol) added in a controlled manner such as to maintain the temperature below 20° C. A precipitate was observed so further water (5 L) and tert-butyl methyl ether (1.5 L) were added to solubilise the reaction mixture. The biphasic mixture was separated. The organic layer was basified with 2M aqueous solution of sodium hydroxide (3.5 L) and stirred vigorously for 18 hours. The aqueous layer was separated and the remaining organic layer washed with water (1.5 L). The aqueous layers were combined and cooled to 15° C. Isopropyl acetate (5 L) was added followed by controlled addition of a 6M aqueous solution of hydrogen chloride (1.2 L), maintaining the temperature below 17° C. The reaction was stirred for 30 minutes. Solid crystallised out in the reactor so was dissolved in a mixture of ethyl acetate and methanol (~20 L). The solution was stirred at room temperature for 18 hours. The reaction was concentrated in vacuo to afford solid material. Ethyl acetate (5 L) was added and concentrated in vacuo. Further ethyl acetate (5 L) was added and the slurry heated to reflux to give an orange solution. The solution was cooled to 50° C. and heptane (2.5 L) added. A thick slurry was observed that was stirred at room temperature for 18 hours. The solid was filtered and dried on a sinter for 3 hours before drying in vacuo at 40° C. for 18 hours to afford the title compound as a white crystalline solid (1.07 Kg, 73% yield).

$^1$HNMR (CDCl$_3$): δ 3.1 (m, 2H), 4.6 (m, 2H), 4.7 (m, 2H), 5.1 (m, 2H), 7.2-7.4 (m, 5H).

Preparation 26

2-{3-[(tert-Butylsulfinyl)amino]oxetan-3-yl}propanoic acid

Methyl 2-{3-[(tert-butylsulfinyl)amino]oxetan-3-yl}propanoate (Preparation 33, 1.25 g, 4.746 mmol) was stirred in methanol (15 mL) and a 1M aqueous solution of sodium hydroxide (15 mL) for 3 hours at room temperature. The reaction was concentrated in vacuo and partitioned between diethyl ether and water. The pH of the aqueous layer was adjusted to pH3 with potassium hydrogen sulphate and extracted with dichloromethane. The organic layer was dried over MgSO$_4$ and concentrated in vacuo to afford the title compound that was used without purification in the next step.

Preparation 27

2-{3-[(tert-Butylsulfinyl)amino]oxetan-3-yl}butanoic acid

Methyl 2-{3-[(tert-butylsulfinyl)amino]oxetan-3-yl}butanoate (Preparation 35, 2.89 g, 10.42 mmol) was stirred in methanol (30 mL) and a 1M aqueous solution of sodium hydroxide (30 mL) for 18 hours at room temperature. The reaction was concentrated in vacuo and partitioned between diethyl ether and water. The pH of the aqueous layer was adjusted to pH3 with potassium hydrogen sulphate and extracted with dichloromethane. The organic layer was dried over MgSO$_4$ and concentrated in vacuo to afford the title compound that was used without purification in the next step.

Preparation 28

2-(3-{[(Benzyloxy)carbonyl]amino}oxetan-3-yl)propanoic acid

Ethyl 2-(3-{[(benzyloxy)carbonyl]amino}oxetan-3-yl)propanoate (Preparation 29, 43 g, 140 mmol) was stirred in methanol (200 mL) and a 1M aqueous solution of sodium hydroxide (200 mL) for 18 hours at room temperature. The reaction was concentrated in vacuo and partitioned between diethyl ether and water. The pH of the aqueous layer was adjusted to pH3 with potassium hydrogen sulphate and extracted with dichloromethane. The organic layer was dried over MgSO$_4$ and concentrated in vacuo to afford the title compound that was used without purification in the next step.

Preparation 29

Ethyl 2-(3-{[(benzyloxy)carbonyl]amino}oxetan-3-yl)propanoate

To a solution of ethyl 2-{3-[(tert-butylsulfinyl)amino]oxetan-3-yl}propanoate (Preparation 34, 40 g, 140 mmol) in methanol (400 mL) at 0° C. was added a 4M solution of hydrogen chloride in 1,4-dioxane (72 mL). After 2 hours, a 4M aqueous solution of sodium hydroxide (400 mL) was added drop-wise until pH 7 was achieved whilst maintaining the temperature at 0° C. The methanol was removed in vacuo. The resulting solution was stirred with tetrahydrofuran (150 mL) and a 1M aqueous solution of sodium hydrogen carbonate (180 mL) at 0° C. Benzyl chloroformate (33.7 g, 187 mmol) was added and the reaction mixture stirred at room temperature for 18 hours. The organics were removed in vacuo and the resulting solution extracted with dichloromethane. The organic layer was dried over $MgSO_4$, filtered and concentrated in vacuo. The resulting residue was purified by silica gel column chromatography to afford the title compound.

Preparation 30

Ethyl (3-aminooxetan-3-yl)acetate

Ethyl oxetan-3-ylideneacetate (Preparation 38, 781 g, 5.49 mol) was dissolved in 2M ammonia in ethanol (8.24 L) and heated to 100° C. in a bomb for 5 hours. The reaction was concentrated in vacuo to afford the title compound as a mobile oil (750 g, 100% yield).
$^1$HNMR ($CDCl_3$): δ 1.25 (t, 3H), 2.0 (br s, 2H), 2.85 (s, 2H), 4.2 (q, 2H), 4.5 (d, 2H), 4.55 (d, 2H).

Preparation 31

Ethyl (3-aminotetrahydrofuran-3-yl)acetate

Ethyl (2Z)-dihydrofuran-3(2H)-ylideneacetate (Preparation 36, 1.29 g, 8.25 mmol) was stirred in 1,4-dioxane (7 mL) in a microwave vial. A solution of 7M ammonia in methanol (5 mL) was added and the reaction heated for 4 hours at 150° C. in a Biotage Initiator™ microwave. The reaction was concentrated in vacuo, but later deemed not to have reached completion. A solution of 7M ammonia in methanol (7 mL) was added and the reaction heated again for 3 hours at 150° C. in the microwave. A further portion of 7M ammonia in methanol (3 mL) was added and the reaction heated for a further 2 hours. The reaction was concentrated in vacuo to afford the title compound along with the methyl ester where trans-esterification had occurred. The material was used without further purification in the next step.

Preparation 32

Ethyl (3-aminotetrahydro-2H-pyran-3-yl)acetate

Ethyl (2Z)-dihydro-2H-pyran-3(4H)-ylideneacetate (Preparation 37, 1.21 g, 7.11 mmol) was stirred in 1,4-dioxane (7 mL) in a microwave vial. A solution of 7M ammonia in methanol (5 mL) was added and the reaction heated for 3 hours at 150° C. in a Biotage Initiator™ microwave. A further solution of 7M ammonia in methanol (2 mL) was added and the reaction heated again for 2 hours at 150° C. in the microwave. The reaction was concentrated in vacuo and the residue dissolved in a further portion of 7M ammonia in methanol (10 mL) and heated for a further 5 hours at 150° C. in the microwave. The reaction was concentrated in vacuo to afford the title compound along with the methyl ester where trans-esterification had occurred. The material was used without further purification in the next step.

Preparation 33

Methyl 2-{3-[(tert-butylsulfinyl)amino]oxetan-3-yl}propanoate

Methyl propionate (2.71 g, 30.8 mmol) was dissolved in anhydrous THF (90 mL) and cooled to −78° C. under nitrogen. LDA (2M solution in THF, 15 mL, 30 mmol) was added drop-wise. After 1 hour at −78° C., a solution of 2-methyl-N-oxetan-3-ylidenepropane-2-sulfinamide (Preparation 39, 1.35 g, 7.703 mmol) in anhydrous THF (10 mL) was added. The reaction was gradually warmed to room temperature and stirred for 18 hours. The reaction was quenched with a saturated aqueous solution of ammonium chloride and extracted with ethyl acetate. The organic layer was dried over $MgSO_4$ and concentrated in vacuo. The residue was purified by silica gel column chromatography to afford the title compound as an oil (1.276 g, 63% yield).
$^1$HNMR ($CDCl_3$): δ 1.25 (s, 9H), 1.3-1.4 (m, 3H), 3.25 (m, 1H), 3.7 (m, 3H), 4.2 (br s, 0.4H), 4.45 (br s, 0.6H), 4.55 (m, 1.1H), 4.6 (m, 0.9H), 4.75 (d, 0.6H), 4.85-5.0 (m, 1.4H).

Preparation 34

Ethyl 2-{3-[(tert-butylsulfinyl)amino]oxetan-3-yl}propanoate

N,N-diisopropylamine (78 g, 770 mmol) was dissolved in anhydrous THF (200 mL) and cooled to −78° C. under nitrogen. Butyl lithium (2.5M solution in hexane, 297 mL, 743 mmol) was added drop-wise. The reaction was removed from the cooling bath for 30 minutes, then re-cooled to −78° C. A solution of ethyl propionate (72.8 g, 713 mmol) in anhydrous THF (200 mL) was added drop-wise and the reaction allowed to stir at room temperature for 1 hour. The reaction was cooled to −78° C. once again and a solution of 2-methyl-N-oxetan-3-ylidenepropane-2-sulfinamide (Preparation 39, 50 g, 285 mmol) in anhydrous THF (200 mL) was added drop-wise. The reaction was stirred at between −40° C. and −60° C. for 4 hours before being quenched with a saturated aqueous solution of ammonium chloride and extracted with ethyl acetate. The organic layer was dried over $MgSO_4$ and concentrated in vacuo. Purification by silica gel column chromatography (ethyl acetate elution) was not successful. The title compound was obtained as a yellow oil (40 g, 51% yield) and used without further purification.

Preparation 35

Methyl 2-{3-[(tert-butylsulfinyl)amino]oxetan-3-yl}butanoate

Methyl butyrate (5.67 g, 55.5 mmol) was dissolved in anhydrous THF (100 mL) and cooled to −78° C. under nitrogen. LDA (2M solution in THF 27.1 mL, 54.2 mmol) was added drop-wise. After 1 hour at −78° C., a solution of 2-methyl-N-oxetan-3-ylidene-propane-2-sulfinamide (Preparation 39, 2.43 g, 13.88 mmol) in anhydrous THF (10 mL) was added. The reaction was gradually warmed to room temperature and stirred for 18 hours. The reaction was quenched with a saturated aqueous solution of ammonium chloride and extracted with ethyl acetate. The organic layer was dried over $MgSO_4$ and concentrated in vacuo. The residue was purified by silica gel column chromatography to afford the title compound as an oil (2.89 g, 75% yield).
$^1$HNMR ($CDCl_3$): δ 1.00 (m, 3H), 1.25 (s, 9H), 1.6-2.0 (m, 2H), 3.0 (m, 1H), 3.7 (m, 3H), 4.3 (br s, 0.5H), 4.50 (m, 1H), 4.55 (br s, 0.5H), 4.6 (m, 0.5H), 4.65 (m, 1H), 4.9 (m, 0.5H), 4.95 (m, 1H).

Preparation 36

Ethyl (2Z)-dihydrofuran-3(2H)-ylideneacetate

Method H

Sodium hydride (60% dispersion in oil, 0.65 g, 16.3 mmol) was cooled to 0° C. under nitrogen before adding anhydrous THF (20 mL). Triethyl phosphonoacetate (3 mL, 15.1 mmol) was added slowly over 40 minutes to control gas evolution. A solution of 3-oxo-tetrahydrofuran (1 g, 11.62 mmol) in anhydrous THF (2 mL) was added and the reaction gradually warmed to room temperature and stirred for 18 hours. The reaction was concentrated in vacuo and the residue partitioned between ethyl acetate (3×50 mL) and water (30 mL). The organic layer was dried over MgSO$_4$ and concentrated in vacuo. The residue was purified by silica gel column chromatography (0-50% ethyl acetate in heptane gradient elution) to afford the title compound as an oil (1.29 g, 71% yield).

$^1$HNMR (CDCl$_3$): δ 1.3 (m, 3H), 2.7 (m, 1H), 3.05 (m, 0.7H), 3.2 (m, 0.3H), 3.9 (t, 1H), 3.95 (t, 0.7H), 4.15 (m, 2H), 4.4 (m, 0.7H), 4.6-4.7 (m, 0.6H), 4.75 (m, 1H), 5.7-5.85 (m, 1H).

LCMS (2 min) Rt=1.23 min MS m/z 157 [MH]$^+$

The following Preparation 37 was prepared by methods analogous to Method H as described for Preparation 36 above. Unless otherwise noted, preparation details are as described for the method referred to.

Preparation 37

Ethyl (2Z)-dihydro-2H-pyran-3(4H)-ylideneacetate

Prepared by Method H using dihydropyran-3-one (1 g, 9.99 mmol) to afford the title compound as an oil (1.214 g, 71% yield).

$^1$HNMR (CDCl$_3$): δ 1.25 (m, 3H), 1.8 (m, 2H), 2.2 (m, 1H), 3.0 (m, 1H), 3.75 (m, 2H), 4.0 (s, 1H), 4.1 (m, 2H), 4.7 (s, 1H), 5.65 (m, 1H).

LCMS (2 min) Rt=1.33 min MS m/z 171 [MH]$^+$

Dihydropyran-3-one can be prepared using the literature procedure *Tet.*, 2004, 60, 46, 10411.

Preparation 38

Ethyl oxetan-3-ylideneacetate

To a solution of (carbethoxymethylene)triphenylphosphorane (1.95 Kg, 5.61 mol) in dichloromethane (4 L) at 0° C. was added over 1 hour, a solution of 3-oxetanone (400 g, 5.55 mol) in dichloromethane (2 L) maintaining the temperature below 10° C. The reaction was warmed gradually to room temperature and stirred for 1.5 hours. The reaction was warmed to 30° C. and dichloromethane (~4 L) removed in vacuo. Heptane (5 L) was added and the mixture distilled under vacuum for a further 1 hour. Further heptane (2.5 L) was added, the temperature increased to 50° C. and the reaction continued to be distilled under vacuum for a further 2 hours. The mixture was cooled to 0° C. and aged for 1 hour at atmospheric pressure. The solid was collected by filtration and washed with heptane (2×2.5 L). The pale yellow filtrate was concentrated in vacuo to afford the title compound as a pale yellow mobile liquid (757 g, 96% yield).

$^1$HNMR (CDCl$_3$): δ 1.25 (t, 3H), 4.2 (q, 2H), 5.3 (m, 2H), 5.5 (m, 2H), 5.65 (m, 1H).

Preparation 39

2-Methyl-N-oxetan-3-ylidenepropane-2-sulfinamide

3-Oxetanone (3 g, 41.63 mmol), tert-butyl sulfinamide (5.55 g, 45.8 mmol) and titanium (IV) ethoxide (13.5 mL, 62.4 mmol) were stirred in THF (200 mL) at 40° C. for 72 hours. The mixture was cooled to room temperature and poured into a rapidly stirred aqueous solution of saturated sodium chloride (200 mL). The resulting suspension was filtered through Celite© and the filter cake washed with ethyl acetate. The organic layer was separated and washed with brine, then dried over MgSO$_4$ and concentrated in vacuo. The residue was purified by silica gel column chromatography to afford the title compound as an oil (1.37 g, 19% yield).

$^1$HNMR (CDCl$_3$): δ 1.3 (s, 9H), 5.4-5.5 (m, 2H), 5.65 (m, 1H), 5.8 (m, 1H).

Preparation 40

2-Bromo-1-[4-(pentafluoro-λ$^6$-sulfanyl)phenyl]ethanone

To a solution of 1-[4-(pentafluoro-λ$^6$-sulfanyl)phenyl]ethanone (Preparation 41, 0.6 g, 2.44 mmol) in THF (20 mL) at 0° C. was added trimethylphenylammonium tribromide (0.962 g, 2.56 mmol). After stirring for 2 hours at 0° C. the reaction was quenched with a saturated aqueous solution of sodium hydrogen carbonate. The reaction was extracted with ethyl acetate and dried over MgSO$_4$ before concentrating in vacuo to afford the title compound that was used without further purification.

Preparation 41

1-[4-(Pentafluoro-λ$^6$-sulfanyl)phenyl]ethanone

To a solution of N-methoxy-N-methyl-4-(pentafluoro-λ$^6$-sulfanyl)benzamide (Preparation 42, 3.0 g, 10.3 mmol) in THF (100 mL) at 0° C. was added drop-wise methyl lithium (1.5M solution, 10.3 mL, 15.5 mmol). The reaction was stirred at 0° C. for 2 hours, then quenched with a saturated aqueous solution of ammonium acetate. The reaction was extracted with ethyl acetate and dried over MgSO$_4$ before concentrating in vacuo to afford the title compound that was used without further purification.

$^1$HNMR (CDCl$_3$): δ 2.65 (s, 3H), 7.9 (d, 2H), 8.05 (d, 2H).

Preparation 42

N-Methoxy-N-methyl-4-(pentafluoro-λ$^6$-sulfanyl) benzamide 4-(Pentafluoro-λ$^6$-sulfanyl)benzoyl chloride (1.00 g, 3.751 mmol), O,N-dimethyl-hydroxylamine hydrochloride (0.402 g, 4.13 mmol), and triethylamine (0.835 g, 8.25 mmol) were stirred in dichloromethane for 2 hours at room temperature. The reaction was concentrated in vacuo and diethyl ether added. The solid was collected by filtration and purified by silica gel column chromatography to afford the title compound as a solid (0.557 g, 51% yield).

LCMS (2 min) Rt=1.56 min MS m/z 292 [MH]$^+$ $^1$HNMR (CDCl$_3$): δ 3.4 (s, 3H), 3.55 (s, 3H), 7.8 (m, 4H).

Assay Method

The ability of the imidazole derivatives of the formula (I) to inhibit the Na$_V$1.8 channel may be measured using the assay described below.

HEK cells stably transfected with hNav1.8, purchased from Millipore (Millipore Corp., Billerica, Mass. 01821), were maintained according to manufacturer's instructions. For electrophysiological studies, cells were removed from the culture flask by brief trypsinization and re-plated at low density onto glass cover slips. Cells were typically used for electrophysiological experiments within 24 to 72 h after plating.

Electrophysiological Recording

Cover slips containing HEK cells expressing hNav1.8 were placed in a bath on the stage of an inverted microscope and perfused (approximately 1 mL/min) with extracellular solution of the following composition: 138 mM NaCl, 2 mM CaCl2, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hNav1.8 currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hNav1.8 were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (≤0.3% dimethyl sulfoxide) was found to have no significant effect on hNav1.8 sodium currents.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or $V_{1/2}$). Compounds were tested for their ability to inhibit hNav1.8 sodium channels by activating the channel with a 20 msec voltage step to 0 mV following an 8 second conditioning prepulse to the empirically determined $V_{1/2}$. Compound effect (% inhibition) was determined by difference in current amplitude before and after application of test compounds. For ease of comparison, "estimated IC-50" values were calculated from single point electrophysiology data by the following equation, (tested concentration, uM)×(100−% inhibition/% inhibition). Inhibition values <20% and >80% were excluded from the calculation.

In some cases electrophysiological assays were conducted with PatchXpress 7000 hardware and associated software (Molecular Devices Corp). All assay buffers and solutions were identical to those used in conventional whole-cell voltage clamp experiments described above. hNav1.8 cells were grown as above to 50%-80% confluency and harvested by trypsinization. Trypsinized cells were washed and resuspended in extracellular buffer at a concentration of 1×10$^6$ cells/mL. The onboard liquid handling facility of the PatchXpress was used for dispensing cells and application of test compounds. Determination of the voltage midpoint of inactivation was as described for conventional whole-cell recordings. Cells were then voltage-clamped to the empirically determined $V_{1/2}$ and current was activated by a 20 msec voltage step to 0 mV.

Estimated IC$_{50}$ values for the compounds of formula I exemplified above are as follows.

| Example No. | Na$_V$1.8 EIC$_{50}$ (μM) |
|---|---|
| 1 | 0.19 |
| 2 | 0.36 |
| 3 | 0.26 |
| 4 | 0.36 |
| 5 | 0.48 |
| 6 | 0.92 |
| 7 | 0.40 |
| 8 | 0.057 |
| 9 | 0.026 |
| 10 | 0.0033 |
| 11 | 0.009 |
| 12 | 0.0097 |
| 13 | 0.0078 |
| 14 | 0.051 |
| 15 | 0.011 |
| 16 | 0.032 |
| 17 | 0.075 |

Where replicate experiments were conducted resulting in multiple sets of data for a test compound, the data presented represent the average value from all replicate experiments.

The invention claimed is:

1. A compound according to formula (I)

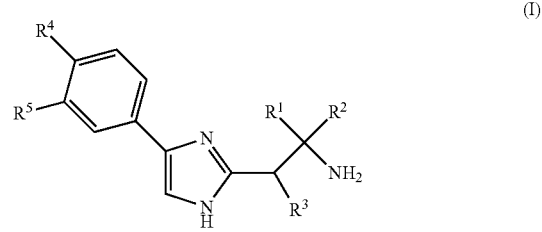

or a tautomer thereof, or a pharmaceutically acceptable salt of said compound or tautomer, wherein:
R$^1$ and R$^2$, together with the carbon to which they are attached, form a 4- to 7-membered ring, wherein:
one member of said ring is O; and
the remaining members of said ring are CR$^6$R$^7$, which may be the same or different at each occurrence;
R$^3$ is selected from the group consisting of H, (C$_1$-C$_3$)alkyl, cyclopropyl, cyclopropyl-CH$_2$—, —CH$_2$OH, —CH$_2$OCH$_3$, (C$_1$-C$_3$)fluoroalkyl, —OH, —OCH$_3$, F, —NH$_2$, NHCH$_3$, —N(CH$_3$)$_2$ and —NHC(O)CH$_3$;
R$^4$ is selected from the group consisting of —CF$_3$, —OCF$_3$, —OCHF$_2$, Cl and —SF$_5$;
R$^5$ is selected from the group consisting of H and —CH$_3$; and $R^6$ and $R^7$ are independently selected from the group consisting of H, $CH_3$—, —OH, —$OCH_3$, F, —$NH_2$, —$NHCH_3$ and —$N(CH_3)_2$.

2. The compound of formula (I) or a tautomer thereof, or a pharmaceutically acceptable salt of said compound or tautomer, according to claim 1, wherein:

$R^1$ and $R^2$, together with the carbon to which they are attached, form a 4- to 7-membered ring of formula

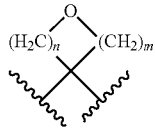

wherein m is 1, 2 or 3 and n is 1 or 2.

3. The compound of formula (I) or a tautomer thereof, or a pharmaceutically acceptable salt of said compound or tautomer, according to claim 2, wherein m is 1 and n is 1.

4. The compound of formula (I) or a tautomer thereof, or a pharmaceutically acceptable salt of said compound or tautomer, according to claim 1, wherein:

$R^3$ is selected from the group consisting of H and ($C_1$-$C_3$) alkyl wherein said $C_1$-$C_3$ alkyl is selected from the group consisting of methyl, ethyl, n-propyl and isopropyl.

5. The compound of formula (I) or a tautomer thereof, or a pharmaceutically acceptable salt of said compound or tautomer, according to claim 1, wherein:

$R^5$ is H.

6. The compound of formula (I) according to claim 1, wherein the compound is selected from:

3-({4-[4-(Trifluoromethoxy)phenyl]-1H-imidazol-2-yl}methyl)tetrahydro-2H-pyran-3-amine, 3-{[4-(4-Chloro-3-methylphenyl)-1H-imidazol-2-yl]methyl}oxetan-3-amine, 3-({4-[4-(Difluoromethoxy)phenyl]-1H-imidazol-2-yl}methyl)oxetan-3-amine, 3-({4-[4-(Pentafluoro-$\lambda^6$-sulfanyl)phenyl]-1H-imidazol-2-yl}methyl)oxetan-3-amine, 4-({4-[4-(Trifluoromethoxy)phenyl]-1H-imidazol-2-yl}methyl)tetrahydro-2H-pyran-4-amine, 3-({4-[4-(Trifluoromethoxy)phenyl]-1H-imidazol-2-yl}methyl)oxetan-3-amine, 3-(1-{4-[4-(Trifluoromethoxy)phenyl]-1H-imidazol-2-yl}ethyl)oxetan-3-amine, 3-[(1S)-1-{4-[4-(Trifluoromethoxy)phenyl]-1H-imidazol-2-yl}ethyl]oxetan-3-amine, 3-[(1R)-1-{4-[4-(Trifluoromethoxy)phenyl]-1H-imidazol-2-yl}ethyl]oxetan-3-amine, 3-(1-{4-[4-(Trifluoromethyl)phenyl]-1H-imidazol-2-yl}ethyl)oxetan-3-amine, 3-[(1S)-1-{4-[4-(Trifluoromethyl)phenyl]-1H-imidazol-2-yl}ethyl]oxetan-3-amine, 3-[(1R)-1-{4-[4-(Trifluoromethyl)phenyl]-1H-imidazol-2-yl}ethyl]oxetan-3-amine, 3-(1-{4-[4-(Trifluoromethoxy)phenyl]-1H-imidazol-2-yl}propyl)oxetan-3-amine, or a tautomer thereof, or a pharmaceutically acceptable salt of said compound or tautomer.

7. A pharmaceutical composition comprising a compound of formula (I) or a tautomer thereof, or a pharmaceutically acceptable salt of said compound or tautomer, as defined in claim 1, and a pharmaceutically acceptable carrier.

8. The pharmaceutical composition of claim 7 wherein the composition is adapted for topical administration.

9. The pharmaceutical composition of claim 7 wherein the composition is adapted for ocular administration.

10. The pharmaceutical composition of claim 7 which further comprises one or more additional therapeutic agents.

11. A method of treating pain, comprising administering a therapeutically effective amount of a compound of formula (I) or a tautomer thereof, or a pharmaceutically acceptable salt of said compound or tautomer, as defined in claim 1, to a subject in need of such treatment.

* * * * *